US012599564B2

(12) United States Patent
Tian et al.

(10) Patent No.: US 12,599,564 B2
(45) **Date of Patent: *Apr. 14, 2026**

(54) ANTIDIABETIC PHARMACEUTICAL COMPOSITIONS

(71) Applicant: ELITE PHARMACEUTICAL SOLUTION INC., Princeton, NJ (US)

(72) Inventors: Wu Tian, Princeton, NJ (US); Yan Wang, Princeton, NJ (US); Henry Tian, Princeton, NJ (US)

(73) Assignee: ELITE PHARMACEUTICAL SOLUTION INC., Princeton, NJ (US)

( * ) Notice: Subject to any disclaimer, the term of this patent is extended or adjusted under 35 U.S.C. 154(b) by 250 days.

This patent is subject to a terminal disclaimer.

(21) Appl. No.: 18/195,920

(22) Filed: May 10, 2023

(65) Prior Publication Data

US 2023/0277465 A1 Sep. 7, 2023

Related U.S. Application Data

(63) Continuation-in-part of application No. 17/028,403, filed on Sep. 22, 2020, now Pat. No. 11,684,596.

(51) Int. Cl.
| | |
|---|---|
| *A61K 9/24* | (2006.01) |
| *A61K 9/00* | (2006.01) |
| *A61K 9/28* | (2006.01) |
| *A61K 31/155* | (2006.01) |
| *A61K 31/4985* | (2006.01) |
| *A61K 45/06* | (2006.01) |

(52) U.S. Cl.
CPC ............ *A61K 9/209* (2013.01); *A61K 9/0053* (2013.01); *A61K 9/2866* (2013.01); *A61K 31/155* (2013.01); *A61K 31/4985* (2013.01); *A61K 45/06* (2013.01)

(58) Field of Classification Search
CPC .. A61K 31/155; A61K 9/0004; A61K 9/0053; A61K 9/209; A61K 9/284; A61K 9/2853; A61K 9/2866; A61K 31/40
See application file for complete search history.

(56) References Cited

U.S. PATENT DOCUMENTS 4,783,337 A * 11/1988 Wong .................. A61K 9/0004
428/913
2010/0323011 A1* 12/2010 Pourkavoos ........... A61K 9/209
514/249

* cited by examiner

*Primary Examiner* — Jianfeng Song

(57) ABSTRACT

An oral dosage form of an antidiabetic pharmaceutical composition comprises a metformin-containing core portion, an outer portion that comprises a non-biguanide antidiabetic agent such as sitagliptin, and a controlled membrane film sandwiched therebetween. The controlled membrane film is provided with at least one passageway allowing core-residing metformin to release out when the oral dosage form is in an aqueous environment, such as in the gastrointestinal (GI) tract of a subject. The oral dosage form has a dissolution profile such that upon dissolving in a medium with a pH of approximately 6.8 at approximately 37° C., less than 15% of the metformin is released at approximately 1 hours, and approximately 45-99% of the metformin is released at approximately 12 hours. The oral dosage form can provide a maximum plasma concentration of the metformin from approximately 7.5 to 15 hours after single-dose oral administration.

11 Claims, 4 Drawing Sheets

ANTIDIABETIC PHARMACEUTICAL COMPOSITIONS

CROSS-REFERENCE TO RELATED APPLICATION

The present application is a continuation-in-part application of, and claims priority to, U.S. patent application Ser. No. 17/028,403 filed on Sep. 22, 2020 and pending, whose disclosure is hereby incorporated by reference in its entirety.

TECHNICAL FIELD

The present disclosure is directed generally to pharmaceutical compositions for treating Type 2 diabetes, and specifically to pharmaceutical compositions comprising a controlled release form of metformin or pharmaceutically acceptable salts thereof in a core, which is further coated with an immediate-release form of the DPP-4 inhibitor sitagliptin or a pharmaceutically acceptable salt thereof. This present disclosure is further directed to processes for preparing such pharmaceutical compositions, and to methods for treating Type 2 diabetes with such pharmaceutical compositions.

BACKGROUND

Type 2 diabetes, also known as hyperglycemia, is a chronic and progressive disease that has been identified as a world epidemic affecting approximately 9% of the world population. Type 2 diabetes is primarily caused by endocrine defects or deficiencies such as insulin resistance and impaired insulin secretion.

Treatment of Type 2 diabetes typically begins with diet and exercise, followed by oral antidiabetic monotherapy. Currently there are a variety of types/classes of antidiabetic medications that can be administered for oral antidiabetic monotherapy, including biguanides, dipeptidyl peptidase 4 (DPP-4) inhibitors, sulfonylureas, meglitinides, thiazolidinediones, sodium-glucose transporter 2 (SGLT2) Inhibitors, and alpha-glucosidase inhibitors, etc.

As an approved first line of antidiabetic agent, metformin is a biguanide that improves glucose tolerance in patients with Type 2 diabetes, lowering both basal and postprandial plasma glucose. Metformin decreases hepatic glucose production, decreases intestinal absorption of glucose, and improves insulin sensitivity by increasing peripheral glucose uptake and utilization. Metformin does not produce hypoglycemia in patients with type 2 diabetes or in healthy subjects except in special circumstances and does not cause hyperinsulinemia. With metformin therapy, insulin secretion remains unchanged while fasting insulin levels and daylong plasma insulin response may decrease.

DPP-4 inhibitors are a class of oral hypoglycemics that block the enzyme dipeptidyl peptidase-4 (DPP-4), whose working mechanism is to slow the inactivation of incretin hormones (e.g. GLP-1 and GIP) to increase their levels, thereby inhibiting glucagon release, increasing insulin secretion, and consequently decreasing blood glucose levels. Sitagliptin was the first agent of the DPP-4 inhibitors that obtained the FDA approval in 2006. Other agents in the class that also obtained FDA approval include saxagliptin (approved in 2009), linagliptin (approved in 2011), and alogliptin (approved in 2013). In addition, the following DPP-4 inhibitors have also obtained approval from, or under clinical trials in, other countries or regions, including vildagliptin (by EU), gemigliptin and evogliptin (both by South Korea), anagliptin, teneligliptin, trelagliptin, and omarigliptin (all by Japan), gosogliptin (by Russia), dutogliptin and berberine (under clinical trial). Herein throughout the disclosure, the term "DPP-4 inhibitor", can include vildagliptin (LAF-237), sitagliptin (MK-0431), sitagliptin phosphate, saxagliptin ((BMS-477118), GSK-823093, PSN-9301, SYR-322, SYR-619, TA-6666, TS-021, GRC-8200, GW-825964X, KRP-104, DP-893, ABT-341, ABT-279, or another salt thereof, or those compounds as described in WO2003074500, WO2003106456, WO2004037169, WO200450658, WO2005058901, WO2005012312, WO2005/012308, WO2006039325, WO2006058064, PCT/EP2005/007821, PCT/EP2005/008005, PCT/EP2005/008002, PCT/EP2005/008004, PCT/EP2005/008283, DE 10 2005 012874.2, DE 10 2005 012873.4, JP2006160733, WO2006071752, WO2006065826, WO2006078676, WO2006073167, WO2006068163, WO2006090915, WO2006104356, WO2006127530, WO2006111261, WO2007015767, WO2007024993, and WO2007029086.

Sulfonylureas act by increasing insulin release from the beta cells in the pancreas, primarily by closing ATP-sensitive $K^+$ channels on the cell membrane of pancreatic beta cells, which depolarizes the cells, causes a rise in intracellular calcium and increased fusion of insulin granule with the cell membrane, in turn leading to the increased secretion of mature insulin. Agents in this drug class include glibenclamide (glyburide), glibornuride, gliclazide, glipizide, gliquidone, glisoxepide and glyclopyramide, among other sulfonylureas of earlier generations (e.g. acetohexamide, carbutamide, chlorpropamide, glycyclamide (tolhexamide), etc.). Pharmaceutical compositions containing any of the above mentioned sulfonylureas have been described in U.S. Pat. Nos. 4,696,815, 4,346,709, 5,518,730, 5,100,669, 6,875,793, 5,091,190 and 5,024,843, etc.

Meglitinides represent another class of antidiabetic drugs having a similar working mechanism as sulfonylureas, yet with a weaker binding affinity and a faster dissociation rate. This class includes repaglinide, nateglinide, and mitiglinide, whose description can be found, for example, in EP0147850A2, EP0207331A1, EP196222, EP526171, and U.S. Pat. No. 5,488,510, etc. Side effects include weight gain and hypoglycemia.

Thiazolidinediones, often abbreviated as TZD, are a class of heterocyclic compounds, which work by lowering the insulin resistance, primarily by activating peroxisome proliferator-activated receptors (PPARs), which can modulate the transcription of a specific set of genes, resulting in an increased storage of fatty acids in fat cells, thereby allowing the body to use insulin and glucose better. This class includes pioglitazone, rosiglitazone, and lobeglitazone, which have been described in patent application Nos: EP0306228, EP0008203, EP0508740, WO92/18501, WO93/02079, and U.S. Pat. Nos. 5,104,888 and 5,478,852. Common side effects associated with TZDs include edema, weight gain, macular edema and heart failure. Moreover, they may cause hypoglycemia when combined with other antidiabetic drugs as well as decrease hematocrit and hemoglobin levels. Increased bone fracture risk is another TZD-related side effect.

SGLT2 inhibitors are a class of medications that inhibit reabsorption of glucose in the kidney and therefore lower blood sugar. SGLT2 inhibitors act primarily by inhibiting sodium-glucose transport protein 2 (SGLT2). Agents of this drug class include canagliflozin, ertugliflozin, empagliflozin, atigliflozin, ipragliflozin, tofogliflozin, and dapagliflozin, luseogliflozin, remogliflozin, sergliflozin, etc., as well as pharmaceutically acceptable salts thereof. These above SGLT2-inhibiting compounds, as well as their pharmaceutically acceptable salts, crystalline forms, or formulations, etc., have been described in WO2007128749, WO2011117295, WO2005012326, WO2009035969, WO2005092877, WO2006120208, WO2011039108, WO2003099836, WO2007140191, WO 2008013280, WO2004080990, WO2004007517, WO2005012326 and WO2007114475, etc. They are available as single-ingredient products and in combination with other diabetes medicines such as metformin. Side effects include urinary tract infections, and low blood pressure.

Alpha-glucosidase inhibitors are a class of anti-diabetic drugs that work by preventing the digestion of carbohydrates, thus reducing the impact of dietary carbohydrates on blood sugar. These agents are substantially saccharides that act as competitive inhibitors of membrane-bound alpha-glucosidases enzymes in small intestines, which are needed to digest carbohydrates. Agents in this drug class include acarbose, miglitol, and voglibose, and description of these chemicals, and the pharmaceutically acceptable salts, formulations, or crystalline forms thereof can be found, for example, in EP0638317A1, CN102872062A, WO2005/030698, etc. Common side effects include gastrointestinal side effects such as flatulence and diarrhea.

For any of the anti-diabetic drug classes described above, the formulations are crucial in delivering their ideal pharmaceutical effects when a medicine of interest is administered to a patient. These ideal pharmaceutical effects may take into consideration the pharmaceutical kinetics (PK) and pharmaceutical dynamics (PD) profile of the medicine of interest in a human body.

In one notable example, metformin salts, and notably metformin hydrochloride, are typically highly water-soluble which can, if administered in an uncontrolled manner, frequently cause gastrointestinal (GI) side effects, such as diarrhea, nausea, and vomiting, occurring more than all other oral antidiabetic agents, yet also has limited duration of pharmaceutical effects, given its PK and PD profiles. Although these GI side effects can diminish over time and can be minimized by taking metformin at mealtimes or by careful dose adjustment, they may impair compliance and even lead to discontinued therapy for certain patients.

In view of these issues, several patent documents, including U.S. Pat. Nos. 4,915,952, 5,328,942, 5,451,409, 5,945,125, 6,090,411, 6,210,710, 6,217,903, 6,488,962, and 6,723,340, 6,866,866 and 8,323,692, and International Patent Application Nos.: WO1996026718A2 and WO1997018814A1, have disclosed controlled-release, extended-release, or prolonged-release drug dosage forms of metformin hydrochloride. Such prolonged or controlled release is realized either through limiting the rate by which the surrounding gastric fluid can diffuse through the matrix and reach the drug, dissolve the drug, and diffuse out again with the dissolved drug, or through using a matrix that slowly erodes, thereby continuously exposing fresh drug to the surrounding fluid. As such, the medicine realizes a controlled release into at least a portion within the body defined by the stomach and the upper gastrointestinal (GI) tract, thereby providing continuous and non-pulsating therapeutic levels of metformin hydrochloride to human subjects in need of such treatment over a twelve-hour to twenty-four-hour period.

Similarly, U.S. Pat. Nos. 6,699,871, 7,879,848, 8,093,236, 8,404,727, 8,628,799, 9,181,256, and International Patent Application Nos.: WO2012131005A1 and WO2015128877A1 have disclosed pharmaceutical formulations of DDP-4 inhibitors, such as sitagliptin, saxagliptin, melogliptin, etc., which typically also consider the PK and PD profiles of these DPP-4 inhibitors in human bodies.

Similarly regarding SGLT2 inhibitors, patent Application Nos.: US20150272977A1, US20170258761A1, US20170056365A1, CN106606489A, US20200179328A1, and KR20200047466A, etc., have disclosed pharmaceutical formulations of certain SGLT2 inhibitor, such as canagliflozin, dapagliflozin or empagliflozin, which may also consider their PK/PD profiles in human or other animals.

Different formulations for other types/classes of anti-diabetic drugs (e.g. sulfonylureas, alpha-glucosidase inhibitors, meglitinides, and thiazolidinediones) as described above, which may similarly give consideration of the PK/PD profiles of these drugs, have also been described in patent documents whose lists are skipped herein.

For many Type 2 diabetes patients, it has been observed that these above regimens, if administered individually as antidiabetic therapy, do not sufficiently control glycemia during long-term treatment. Therefore, there has been a requirement for a combination therapy that comprise two or more oral antidiabetic agents, which can exert additive, complementary, and/or synergetic antidiabetic effects for better glycemic control for these Type 2 diabetes patients. Yet co-prescription of two or more oral antidiabetic drugs may result in treatment regimens that are complex and thus difficult for many patients to follow.

As such, combining two or more oral antidiabetic agents into a single tablet provides a potential means of delivering combination therapy without adding to the complexity of patients' daily regimens. Several patents or patent applications have documented such.

U.S. Pat. No. 7,785,627 discloses a pharmaceutical dosage form comprising a biguanide (e.g., metformin hydrochloride or other metformin salts) or a pharmaceutically acceptable salt thereof in combination with a thiazolidinedione (TZD) derivative. U.S. Pat. No. 9,616,028 discloses bilayer tablet formulations comprising a metformin formulation as the first layer, and SGLT2 inhibitor formulation as the second layer. The International Patent Application No.: WO2013131967A1 discloses a combination of metformin hydrochloride, present in an extended release core, and at least one of a DPP-4 inhibitor or a SGLT-2 inhibitor, present in an immediate release coating.

The combination of metformin and/or its salt formulation, and a DPP-4 inhibitor (e.g. sitagliptin, vildagliptin, saxagliptin, denagliptin, etc.) and its salt formulation for a pharmaceutical composition to treat type 2 diabetes has been widely studied and has disclosed in U.S. Pat. No. 9,155,705, U.S. Patent Application No.: 20100330177A1, and International Patent Application Nos.: WO2007078726A2, WO2009099734A1, WO2009111200A1, WO2011098483A1, WO2013110085A1, WO2014167437A1, and WO2014170770A1.

It is noted that on the clinical front, the combination therapies using any two of these above anti-diabetic agents have gone through regulatory approval worldwide. For example, sitagliptin has been given in combination with metformin, sulfonylurea, thiazolidinediones, or as a triple combination with metformin and sulfonylurea or metformin and thiazolidinediones both in the USA and Europe. In the recent years a fix combination of sitagliptin/metformin has also been available. Concomitant administration of sitagliptin with insulin has been approved by FDA and EMA in 2010. Saxagliptin can be used in combination with other oral antidiabetic drugs, such as metformin, sulfonylurea, and thiazolidinediones, both in the USA and in Europe in 2007.

However, one issue associated with many existing pharmaceutical compositions for combination therapy is that each of the two or more oral antidiabetic agents included in the pharmaceutical formulation often have different pharmaceutical kinetics (PK) and pharmaceutical dynamics (PD) profiles, and the formulation for these different pharmaceutical agents is not optimized based on their different PK/PD profiles. Consequently, these existing formulations often do not generate an optimized pharmaceutical effect.

On the one hand, after one such pharmaceutical composition comprising a first effective agent and a second effective agent is orally administered in a human body, the first pharmaceutical agent may be metabolized much faster than the second pharmaceutical agent, consequently these two agents do not exert their antiglycemic effects concomitantly or complementarily to thereby form a synergy to have a maximized antidiabetic effect.

On the other hand, different classes of anti-diabetic drugs may have adverse drug-drug interaction caused by their respective PD profiles. For example, sitagliptin (Januvia) plus a sulfonylurea increases risk for hypoglycemia, whereas since metformin does not directly stimulate insulin secretion, hypoglycemia risk may be lower than for that of other oral anti-diabetes drugs.

In the prior art, many techniques have been used to provide controlled and extended-release pharmaceutical dosage forms in order to maintain therapeutic serum levels of medicaments and to minimize the effects of missed doses of drugs caused by a lack of patient compliance and reduce side effect by reducing the possibility of dumping of drug in gastrointestinal GI system or reducing the over exposing the drug on the surface of the gastrointestinal GI system.

Although vast amounts of research has been performed on controlled or sustained release compositions and in particular on osmotic dosage forms, very little research has been performed in the area of antihyperglycemic drugs, especially when combination of two of antihyperglycemic drugs can produce improved clinical results; and at least one of antihyperglycemic drugs can be on controlled or sustained release compositions and in particular on osmotic dosage forms to increase possible clinical effectiveness and reduce side effect.

SUMMARY OF THE INVENTION

In a first aspect, the present disclosure provides an oral dosage form of a pharmaceutical composition for managing diabetes or prediabetes in a subject.

The oral dosage form comprises a core portion, an outer portion, and a controlled membrane film. The core portion comprises a therapeutically effective amount of metformin or a pharmaceutically acceptable salt thereof (e.g. metformin hydrochloride (HCl), metformin phosphate, etc.), and the outer portion comprises at least one non-biguanide antidiabetic agent (i.e. an antidiabetic agent that does not belong to biguanide drug class to thereby allow a synergy). Each metformin or each non-biguanide antidiabetic agent is at a therapeutically effective amount. The controlled membrane film encapsulates the core portion, and is sandwiched between the core portion and the outer portion. The controlled membrane film is provided with at least one passageway configured to allow the at least one first antidiabetic agent to release out of the core portion therethrough when the oral dosage form is in an aqueous environment, such as in the gastrointestinal (GI) tract of the subject.

In certain embodiments of the oral dosage form of the pharmaceutical composition, the metformin or a pharmaceutically acceptable salt thereof can optionally have a relative amount of approximately 70-90% of the core portion by weight. In addition to the metformin, the core portion may comprise a biguanide other than metformin (e.g. phenformin or buformin, etc.) or a pharmaceutically acceptable salt thereof. As such, the core can further comprise at least one granulation binding polymer. Each of the at least one binding polymer can be selected from hydroxypropyl methylcellulose (HPMC), hydroxyl-propyl cellulose (HPC), hydroxyethyl cellulose (HEC), poly(ethylene) oxide (PEO), polyvinyl alcohol (PVA), povidone (PVP), and co-povidone. Mixtures of the above-mentioned binding agents may also be used. The preferred binding agents are water soluble such as polyvinyl pyrrolidone having a weight average molecular weight of 25,000 to 3,000,000. The binding agent comprises approximately about 0 to about 40% of the total weight of the core and preferably about 3% to about 15% of the total weight of the core. The core should comprise at least one penetration/absorption enhancer. The absorption enhancer can be any type of absorption enhancer commonly known in the art such as a fatty acid, a surfactant, a chelating agent, a bile salt or mixtures thereof. Examples of some preferred absorption enhancers are fatty acids such as capric acid, oleic acid and their monoglycerides, surfactants such as sodium lauryl sulfate, sodium taurocholate and polysorbate 80, chelating agents such as citric acid, phytic acid, ethylenediamine tetraacetic acid (EDTA) and ethylene glycol-big (B-aminoethyl ether-N,N,N,N-tetraacetic acid (EGTA)). The core comprises approximately 0 to about 20% of the absorption enhancer based on the total weight of the core and most preferably about 2% to about 10% of the total weight of the core. In this embodiment the core which comprises the antihyperglycemic drug, the binder which preferably is a pharmaceutically acceptable water soluble polymer and the absorption enhancer is preferably formed by wet granulating the core ingredients and compressing the granules with the addition of a lubricant into a tablet on a rotary press. The core may also be formed by dry granulating the core ingredients and compressing the granules with the addition of a lubricant into tablets or by direct compression. Other commonly known excipients may also be included into the core such as lubricants, pigments or dyes.

Preferably, the metformin or a pharmaceutically acceptable salt thereof in the core portion of the oral dosage form may comprise metformin hydrochloride (metformin HCl), which may have a dosage form of approximately 250-2000 mg. For example, the oral dosage form provided in the oral dosage form may include 250 mg, 500 mg, 750 mg, 1000 mg or 2000 mg, and preferably 500 mg, 750 mg and 1000 mg, of metformin HCl.

According to some embodiments of the oral dosage form where the core portion comprises metformin HCl, the oral dosage form has a dissolution profile such that upon dissolving in a medium with a pH of approximately 6.8 at approximately 37° C. (e.g. under a testing condition where the oral dosage form is tested in a USP Type II apparatus at approximately 50 rpm at approximately 37° C. in 900 ml of a medium having a pH of approximately 6.8), less than 15% of the metformin is released from the oral dosage form at approximately 1 hours; and approximately 45-99% of the metformin is released from the oral dosage form at approximately 12 hours.

Depending on different designs, these above embodiments of the oral dosage form may have different dissolution profiles.

Certain embodiments of the oral dosage form may have a relatively slower dissolution for the core-residing metformin (e.g. Embodiments 7-11 below), such that upon dissolving the oral dosage form in a medium with a pH of approximately 6.8 at approximately 37° C., less than 70% of the metformin is released from the oral dosage form at approximately 12 hours.

Further optionally, upon dissolving the oral dosage form in a medium with a pH of approximately 6.8 at approximately 37° C., approximately 80-95% of the metformin is released from the oral dosage form at approximately 24 hours.

Further optionally, upon dissolving the oral dosage form in a medium with a pH of approximately 6.8 at approximately 37° C., approximately 5-10% of the metformin is released from the oral dosage form at approximately 2 hours.

Further optionally, upon dissolving the oral dosage form in a medium with a pH of approximately 6.8 at approximately 37° C., approximately 30-50% of the metformin is released from the oral dosage form at approximately 8 hours.

Certain embodiments of the oral dosage form may have a relatively faster dissolution for the core-residing metformin (e.g. Embodiments 1-6 below), such that upon dissolving the oral dosage form in a medium with a pH of approximately 6.8 at approximately 37° C., approximately 80-99% of the metformin is released from the oral dosage form at approximately 12 hours.

Further optionally, upon dissolving the oral dosage form in a medium with a pH of approximately 6.8 at approximately 37° C., approximately 15-30% of the metformin is released from the oral dosage form at approximately 2 hours.

Further optionally, upon dissolving the oral dosage form in a medium with a pH of approximately 6.8 at approximately 37° C., approximately 30-55% of the metformin is released from the oral dosage form at approximately 4 hours.

Further optionally, upon dissolving the oral dosage form in a medium with a pH of approximately 6.8 at approximately 37° C., approximately 60-95% of the metformin is released from the oral dosage form at approximately 8 hours.

Optionally, the oral dosage form can be configured to realize a controlled release of the at least one first antidiabetic agent such that upon a single-dose oral administration, the oral dosage form provides a maximum plasma concentration of metformin in the subject from approximately 7.5 to 15 hours after administration.

Optionally in the oral dosage form where the core portion comprises metformin HCl, the oral dosage form is configured to provide a mean maximum plasma concentration ($C_{max}$) of metformin from approximately 0.5*X ng/ml to approximately 1.6*X ng/ml, based on administration of the oral dosage form comprising X mg of metformin HCl, wherein X is in a range of approximately 250-1000. In certain embodiment, the controlled release oral dosage form comprises 1000 mg of metformin HCl, the oral dosage form as such is configured to provides a mean maximum plasma concentration ($C_{max}$) of the drug that is about 500-1600 ng/ml, based on administration of the 1000 mg once-a-day dose of metformin. In another embodiment, the controlled release oral dosage form comprises 500 mg of metformin HCl, the oral dosage form as such is configured to provides a mean maximum plasma concentration ($C_{max}$) of the drug that is about 250-800 ng/ml, based on administration of the 500 mg once-a-day dose of metformin.

Optionally in the oral dosage form where the core portion comprises metformin HCl, the oral dosage form is configured to provide a mean maximum AUC0-t from approximately 7*Y hr*ng/mL to approximately 16*Y hr*ng/mL, based on administration of the oral dosage form comprising Y mg of metformin HCl, wherein Y is in a range of approximately 250-1000. In certain embodiments, the controlled release oral dosage form comprises 1000 mg of metformin HCl, the controlled release dosage form provides a mean $AUC_{0\text{-}24\ hr}$ that is about 7000-16000 ng·hr/ml, based on administration of a 1000 mg once-a-day dose of metformin. In another embodiment, the controlled release oral dosage form comprises 500 mg of metformin HCl, the controlled release dosage form provides a mean $AUC_{0\text{-}24\ hr}$ that is about 3500-8000 ng·hr/ml, based on administration of a 500 mg once-a-day dose of metformin.

In any of the embodiments of the oral dosage form as described above, the controlled membrane film may comprise at least one controlling polymer. Each of the at least one controlling polymer is selected from a cellulose acetate, or a cellulose acetate phthalate. According to some embodiments, the at least one controlling polymer in the controlled membrane film of the oral dosage form of the pharmaceutical composition can be cellulose esters, cellulose diesters, cellulose triesters, cellulose ethers, cellulose acetate phthalate, cellulose acetate, cellulose diacetate, cellulose triacetate, cellulose acetate propionate, and cellulose acetate butyrate. Other suitable polymers are described in U.S. Pat. Nos. 3,845,770, 3,916,899, 4,008,719, 4,036,228 and 411, 210 which are incorporated herein by reference. The most preferred membrane material is selected from CA-320S, CA-398-3, CA398-6, CA 398-10, CA 398-30, CA398-60S. In some specific embodiments, the at least one controlling polymer comprises Cellulose Acetate-398-10. According to some embodiments of the oral dosage form of the pharmaceutical composition, a relative amount of the at least one controlling polymer in the controlled membrane film of the oral dosage form of the pharmaceutical composition can be approximately 1% to 100% of the controlled membrane film by weight. Herein optionally, the relative amount of the at least one controlling polymer can be approximately 1.5% to 5.0% of the tablet by weight. According to some embodiments of the oral dosage form of the pharmaceutical composition, the controlled membrane film further comprises at least one plasticizing agent such as polyethylene glycol, which has a relative amount of approximately 0.1-40% of the controlled membrane film by weight. Herein optionally, the at least one polyglycol can comprise polyethylene glycol (PEG) 3350, which is configured to have a relative amount of approximately 0.1-40% of the controlled membrane film by weight.

In any of the embodiments of the oral dosage form as described above, the at least one non-biguanide antidiabetic agent contained in the outer portion of the oral dosage form can comprise at least one DDP-4 inhibitor, or a pharmaceutically acceptable salt thereof.

According to certain embodiments, the at least one DDP-4 inhibitor comprises one or more of sitagliptin, saxagliptin, linagliptin, alogliptin, vildagliptin, gemigliptin, anagliptin, teneligliptin, trelagliptin, omarigliptin, evogliptin, gosogliptin, dutogliptin, or berberine.

Herein preferably, the at least one non-biguanide antidiabetic agent comprises sitagliptin phosphate, having a dosage form of approximately 25-200 mg and having an immediate release formulation. For example, the oral dosage form provided in the oral dosage form may include 25 mg, 50 mg, 100 mg or 200 mg, and preferably 50 mg or 100 mg, of sitagliptin phosphate.

Optionally in the oral dosage form where the at least one non-biguanide antidiabetic agent in the outer portion comprises sitagliptin phosphate, when the oral dosage form is tested in a USP Type I apparatus at approximately 75 rpm at approximately 37° C. in 900 ml of 0.025 mol/mL sodium chloride solution, the sitagliptin phosphate is configured to exhibit a dissolution profile such that upon contacting the oral dosage form with the medium, more than 85% of the sitagliptin phosphate is released at approximately 60 min after testing (i.e. the oral dosage form contacting the sodium chloride solution in the test). Further preferably, the sitagliptin phosphate exhibits a dissolution profile such that upon contacting the oral dosage form with the medium, more than 25% of the sitagliptin phosphate is released at approximately 10 min after testing.

According to certain embodiments of the oral dosage form, the at least one non-biguanide antidiabetic agent comprises one or more of:

a sulfonylurea or a pharmaceutically acceptable salt thereof;

a meglitinide or a pharmaceutically acceptable salt thereof;

a thiazolidinedione or a pharmaceutically acceptable salt thereof;

a sodium-glucose transporter 2 (SGLT2) inhibitor or a pharmaceutically acceptable salt thereof, or an alpha-glucosidase inhibitor or a pharmaceutically acceptable salt thereof.

Preferably, the at least one non-biguanide antidiabetic agent has an immediate release formulation and comprises one of:

dapagliflozin having a dosage strength of approximately 2.5-10 mg;

empagliflozin having a dosage strength of approximately 2.5-25 mg;

glipizide having a dosage strength of approximately 1.25-10 mg;

glyburide having a dosage strength of approximately 1.25-10 mg;

repaglinide having a dosage strength of approximately 0.5-5 mg;

nateglinide having a dosage strength of approximately 30-60 mg;

pioglitazone having a dosage strength of approximately 15-45 mg;

rosiglitazone having a dosage strength of approximately 1-4 mg;

acarbose having a dosage strength of approximately 12.5-100 mg; or miglitol having a dosage strength of approximately 12.5-100 mg.

According to certain embodiments, the oral dosage form further comprises an inner seal film, which is sandwiched between the core portion and the controlled membrane film, configured to provide a protective coating for the core portion encapsulated therein.

According to certain embodiments, the oral dosage form further comprises an outer seal film coating an outer surface of the outer portion, which is configured to provide a protective coating for the outer portion encapsulated therein.

According to certain embodiments, the oral dosage form further comprises both an inner seal film sandwiched between the core portion and the controlled membrane film and an outer seal film coating an outer surface of the outer portion.

In the above embodiments of the oral dosage form, at least one of the inner seal film or the outer seal film comprises at least one film-forming polymer, each selected from the group consisting of hypromellose, hydroxypropyl methylcellulose (HPMC), hydroxypropylcellulose (HPC), carboxymethylcellulose, polyvinylpyrrolidone (PVP), and polyvinyl alcohol and polyethylene glycol (PEG).

In the above embodiments of the oral dosage form, the inner seal film or the outer seal film has a ratio of approximately 0.4% to 40%, and preferably 2%-10%, by weight of the oral dosage form.

In the above embodiments of the oral dosage form, the inner seal film, the outer seal film, or both, may further comprise at least one of a plasticizers, or a pigment, or a dispersing agent, or an antioxidant.

According to some embodiments of the oral dosage form of the pharmaceutical composition, the at least one passageway is mechanically or optically created in the middle of membrane coated tablets.

As used herein the term passageway includes an aperture, orifice, bore, hole, weakened area or an erodible element such as a gelatin plug that erodes to form an osmotic passageway for the release of the antihyperglycemic drug from the dosage form. A detailed description of the passageway can be found in U.S. Pat. Nos. such as U.S. Pat. Nos. 3,845,770, 3,916,899, 4,034,758, 4,063,064, 4,077,407, 4,088,864, 4,783,337, and 5,071,607 (the disclosures of which are hereby incorporate by reference). In certain embodiments, the passageway is formed by laser drilling. In preferred embodiments of the invention, the dosage form contains one passageway on each side of each tablet in order provide the desired pharmacokinetic parameters of the formulation.

In any of the embodiments of the oral dosage form as described above, there is no limitation to the number of passageways. According to some embodiments, there can be two passageways, which may be respectively arranged on the opposing side of the controlled membrane film. Preferably, each of the two passageways may be arranged within ±5 mm, and preferably within ±2 mm, of a center of each side of the controlled membrane film. Each passageway may have a diameter of approximately 0.30-2.00 mm, and preferably of 0.40-0.60 mm. Each passageway may have a depth of approximately 0.10-2.00 mm, and preferably of 0.30-1.40 mm.

In any of the embodiments of the oral dosage form of the pharmaceutical composition as described above, the subject can be a human, or a mammalian organism that is afflicted by diabetes.

In a second aspect, the present disclosure further provides a method for manufacturing an oral dosage form of a pharmaceutical composition. The oral dosage form can be the oral dosage form of the composition according to any one of the embodiments as described above in the first aspect.

The method can comprise the following steps (A-C):

(A) preparing a core portion comprising at least one first antidiabetic agent;

(B) coating the core portion with a controlled membrane film, wherein the controlled membrane film is provided with at least one passageway configured to allow the at least one first antidiabetic agent to release out of the core portion therethrough;

(C) coating the controlled membrane film with an outer portion comprising at least one second antidiabetic agent.

Optionally, the method comprises a step between step (A) and step (B), comprising:

coating the core portion with an inner seal film, wherein the inner seal film is configured to provide a protective coating for the core portion encapsulated therein.

Optionally, the method comprises a step after step (C), comprising:

coating the outer portion with an outer seal film, wherein the outer seal film is configured to provide a protective coating for the outer portion encapsulated therein.

In step (A) of the method, the core portion comprising the at least one first antidiabetic agent can be formulated by the following sub-steps:

(1) granulation-by dry granulation, wet granulation or a fluid bed granulation;

(2) milling;

(3) mixing; and (4) compression.

Optionally, after sub-step (4) of obtaining the core portion, step (A) further comprises a sub-step (5) of coating the core portion with a seal coating solution, wherein the seal coating solution can be made of hypromellose or hydroxypropyl cellulose and polyethylene glycol or other suitable water-soluble material by first dissolving the hypromellose or hydroxypropyl cellulose and polyethylene glycol. The coating solution was then sprayed onto the core tablets using a pan coater. The seal film constitutes about 2%-10% by weight of the oral dosage form. In step (B) of the method, the controlled membrane film may comprise at least one controlling polymer, each optionally selected from a cellulose acetate or cellulose acetate phthalate polymers; and at least one passageway can then be generated in the controlled membrane film.

According to some embodiments of the method, step (B) of coating the core portion with a controlled membrane film comprises the following sub-steps:

(1) preparing a spray suspension, wherein the spray suspension comprises CA-398-10 and PEG3350; and (2) coating the core portion with the spray suspension to thereby obtain a coated core; and (3) curing the coated core.

In the above embodiments of the method, the above sub-step (3) of curing the coated core comprises:

curing the coated core for approximately at least one hour at 50° C.

In certain embodiments, each of the at least one passageway is formed by laser drilling. In preferred embodiments of the invention, the oral dosage form contains one passageway on each side of each tablet in order provide the desired pharmacokinetic parameters of the formulation, the orifice should be within ±2 mm of the middle of the tablet, diameter of orifice should be between 0.40 to 0.60 mm, and the depth of orifice should be between 0.30 to 1.40 mm.

In certain embodiments of the method, the at least one second antidiabetic agent in the outer portion in step (C) can be prepared such that a suspension for the at least one second antidiabetic agent can be prepared by mixing all the excipients (except Kaolin) and the at least one second antidiabetic agent in the required amount of purified water using a suitable homogenizer until the solids are dissolved. Then the pre-screened (mesh #60) Kaolin powder can be added to the at least one second antidiabetic agent coating suspension and mixed with a suitable mixer and blade until the powder is uniformly dispersed in the coating suspension.

In certain embodiments of the method, the at least one second antidiabetic agent the at least one second antidiabetic agent in the outer portion in step (C) can be prepared such that a solution for the at least one second antidiabetic agent can be prepared by mixing all the excipients and the second antidiabetic agent in the required amount of purified water using a suitable homogenizer until the solids were dissolved. Then the membrane coated tablets can be loaded into a suitable perforated side-vented coating pan with baffles fitted with single or multi spray gun to produce a spray to cover the entire width of the tablet bed; the average weight of warmed uncoated tablet will be determined as the initial starting weight; the second antidiabetic coating suspension or solution can be sprayed onto the tablet bed at a suitable spray rate and atomization pressure; spraying will be continued while monitoring the tablet weight until the required weight gain is obtained.

In certain embodiments of the method where the outer portion of the oral dosage from is further coated with an outer seal film, the outer seal film can be fabricated by the following procedures. Briefly, an outside seal coating solution can be prepared by mixing all the excipients in the required amount of purified water using a suitable homogenizer until the solids are dissolved. The tablets coated with the at least one second antidiabetic agent (i.e. the outer portion) can be loaded into a suitable perforated side-vented coating pan with baffles fitted with single or multi spray gun to produce a spray to cover the entire width of the tablet bed; the average weight of warmed uncoated tablet is determined as the initial starting weight; the seal coating solution will be sprayed onto the tablet bed at a suitable spray rate and atomization pressure; spraying will be continued while monitoring the tablet weight until the required weight gain is obtained.

Throughout the disclosure, the term "tablet" is intended to encompass compressed pharmaceutical dosage formulations of all shapes and sizes, whether coated or uncoated.

The term "pharmaceutically acceptable" as used herein refers to compounds, materials, compositions, and/or dosage forms which are, within the scope of sound medical judgment, suitable for use in contact with tissues of human beings and animals and without excessive toxicity, irritation, allergic response, or any other problem or complication, commensurate with a reasonable benefit/risk ratio.

The terms "pharmaceutical composition" or "dosage form" as used herein are used interchangeably and are defined to mean a pharmaceutical composition, preparation or system in which doses of medicine or active drug are included. Pharmaceutical compositions or dosage forms can be administered by any route of administration known to the skilled in the art, including but not limited to oral, parenteral, pulmonary, rectal, vaginal, nasal and topical.

The term "dosage form" as it is used herein means at least one unit dosage form of the present invention (e.g. the daily dose of the antihyperglycemic agent can be contained in 2 unit dosage forms of the present invention for single once-a-day administration).

The term "oral dosage form" as used herein is defined to mean a dosage form which is administered by mouth, for absorption through the mucous membranes of the mouth and/or, after swallowing, through the gastrointestinal tract. Such oral dosage forms include but are not limited to solutions, syrups, suspensions, emulsions, gels, powders, granules, capsules, tablets, buccal dosage forms and sublingual dosage forms.

The term "therapeutically effective" when used herein is meant to signify an amount of an antidiabetic agent that can reduce blood glucose levels by approximately the same amount as an immediate release reference standard (e.g., Janumet™) or more, when the controlled release dosage form is orally administered to a human patient on a once-a-day basis.

The term "immediate release" (short as "IR"), is defined for the purpose of this present disclosure as the release of an active drug content from an oral dosage form into the gastrointestinal tract within a short period of time after administration, and typically the plasma drug levels also peak shortly after dosing. Accordingly, the term "immediate release dosage forms" is referred to as dosage forms which exhibit an "immediate release" of the active drug, and thus provide a substantially immediate rate of release of the active drug.

The term "controlled release" (short as "CR"), as referred to in the whole disclosure is considered to be interchangeable with the terms "extended release" (short as "ER"), "prolonged release" (short as "PR"), "sustained release" (short as "SR"), and is defined for the purpose of this present disclosure as the release of the active drug over an extended period of time (e.g. from about 12 hours to about 24 hours) compared to an immediate release dosage form, such that plasma concentrations of the active drug are maintained for a longer time at a therapeutic level, and therapeutic benefit is maintained for a prolonged period. Accordingly, the terms "controlled release dosage forms", "immediate release dosage forms", "prolonged release dosage forms", and/or "sustained release dosage forms", are referred to as dosage forms which exhibit an "controlled release", an "immediate release", a "prolonged release", and/or a "sustained release" of the active drug.

Throughout the disclosure, the different formulations of Fortamet are referred to as the extended release dosage form of metformin HCl, which is branded in Andrx Labs and other companies, and has been described in U.S. Pat. No. 6,866,866. The Janumet XR is referred to as a dosage form of sitagliptin and metformin, branded in Merck, and has been described in U.S. Pat. No. 7,759,366.

Throughout the disclosure, the relatively term "approximately", "about", "around", or alike, that is behind a number, is referred to as a description of an actual number that is within 5% of the indicated number. In one illustrating example, "approximately 1.00" can be interpreted that the actual number is between 0.95 and 1.05.

DETAILED DESCRIPTION

Figure 1:
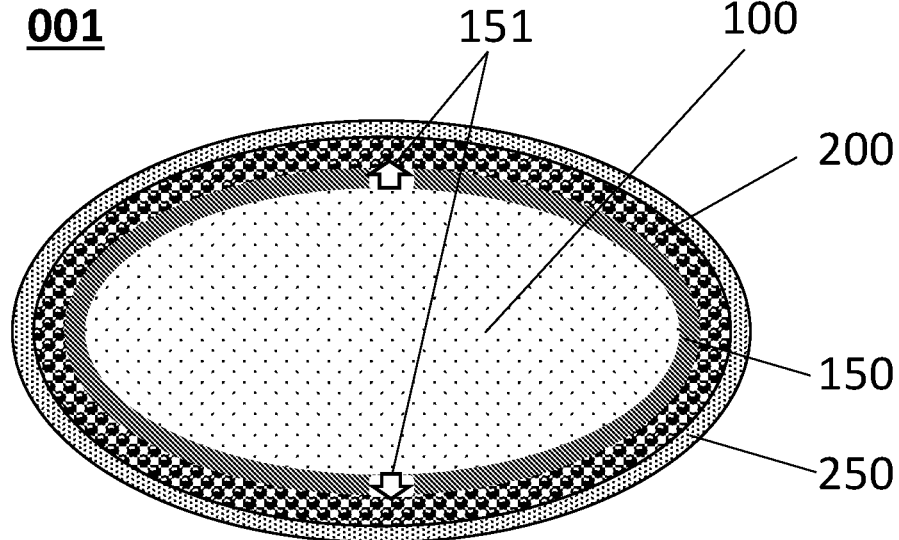
FIG. 1 is a schematic diagram of a dosage form of the pharmaceutical composition according to some embodiments of the disclosure.

In the following, with reference to the above-mentioned drawings of various embodiments disclosed herein, the technical solutions of the various embodiments of the disclosure will be described in a clear and fully understandable way. It is noted that the described embodiments represent merely a portion, but not all, of the embodiments of the disclosure. Based on the described embodiments of the disclosure, those ordinarily skilled in the art can obtain other embodiment(s), which shall come within the scope sought for protection by the disclosure.

In a first aspect, the present disclosure provides a dosage form of a pharmaceutical composition that is specifically used for treating a subject with diabetes or prediabetes.

Herein the dosage form is preferably an oral dosage form that is taken by the subject orally, and the subject can be, but is not limited to, a human, and can also be yet another insulin-producing mammal, such as a monkey, a chimpanzee, a dog, a cat, etc.

In the dosage form disclosed herein, the pharmaceutical composition comprises two or more antidiabetic agents, each having a different action of mechanism and together having an additive, complementary, and/or synergistic effect in glycemic control. According to some embodiments, one of the two or more antidiabetic agents comprises a biguanide or a pharmaceutically acceptable salt thereof. Preferably, the biguanide can be metformin, or a pharmaceutically acceptable salt thereof (e.g. metformin hydrochloride). In addition to the biguanide, the two or more antidiabetic agents in the oral dosage form of the pharmaceutical composition further comprise one or more other types of antidiabetic medications, such as a sulfonylurea, a meglitinide, a thiazolidinedione, a DPP-4 inhibitor, a sodium-glucose transporter 2 (SGLT2) inhibitor, or an alpha-glucosidase inhibitor, etc.

In the dosage form of the pharmaceutical composition, each of the two or more antidiabetic agents can be further configured to have a dosage and/or a formulation that is optimized such that when the dosage form is orally administered in the subject, the two or more antidiabetic agents can complementarily and synergistically exert their respective antiglycemic effects to thereby realize a optimized therapeutic effect on the subject. In other words, the dosage(s) and/or formulation(s) of the two or more antidiabetic agents are respectively optimized in the dosage form so as to allow a maximally synergistic complementation of their respective action of mechanism once the dosage form of the pharmaceutical composition is taken up by the subject. According to some embodiments of the dosage form, the dosages and/or formulations for the two or more antidiabetic agents contained therein are designed or configured to be optimized based on their respective PK/PD profiles in the subject.

In the dosage form of the pharmaceutical composition provided herein, any one of the two or more antidiabetic agents can be configured to be in an immediate-release formulation or alternatively in a controlled release formulation according to their respective PK/PD profiles that have been established.

Regarding the immediate-release formulation of an antidiabetic agent in an oral dosage form of the pharmaceutical composition, the antidiabetic agent can be provided as granules, spheroids, beads, particles, pellets (hereinafter collectively referred to as "multiparticulates"), etc. An amount of the multiparticulates which is therapeutically effective to provide the desired dose of drug over time may be placed in a capsule or may be incorporated in any other suitable oral form.

Regarding the controlled-release formulation of an antidiabetic agent in an oral dosage form of the pharmaceutical composition, it can be realized by arranging the antidiabetic agent at a core of the dosage form, and the core is further coated with a controlled membrane film which is configured to realize a controlled release of the core-residing antidiabetic agent.

FIG. 1 illustrates a structural diagram of an oral dosage form of the pharmaceutical composition according to certain embodiments of the present disclosure. As illustrated in the figure, the oral dosage form 001 of the pharmaceutical composition substantially comprises a core portion 100 comprising at least one first antidiabetic agent and an outer portion 200 comprising at least one second antidiabetic agent.

A controlled membrane film 150 is sandwiched between the core portion 100 and the out portion 200. One or more delivery passageways (e.g. orifices, pores, holes, or alike) 151 are arranged on the controlled membrane film 150, which are configured to provide delivery passageways for the at least one second antidiabetic agent in the core portion 100 to get out of the controlled membrane film 150, so as to realize a controlled release or an extended release thereof. In FIG. 1, only two delivery passageways 151 are shown, yet it is noted that it is for illustration purposes only, and there is no limitation on the number of delivery passageways arranged in the controlled membrane film 150. Optionally, each of the delivery passageways can be further provided with a soluble plug (not shown in the figure), such as a water soluble material (e.g. gelatin) or an enteric material, which is configured to seal the passageways but can dissolve or leach in a water solution (e.g. GI fluid) to thereby open the delivery passageways to allow the at least one first antidiabetic agent in the core portion 100 to release. Herein, the controlled membrane film 150 can comprise from about 1% to about 7%, preferably about 1.5% to about 4%, of the whole oral dosage form in mass weight. In certain preferred embodiments of the disclosure, the dosage form contains two passageways that are configured to provide the desired pharmacokinetic parameters of the formulation.

Herein, the controlled membrane film 150 can be a semipermeable membrane by being permeable to the passage of external fluid such as water and biological fluids and being impermeable to the passage of the antidiabetic drug in the core. As such, the controlled membrane film 150 can comprise at least one insoluble polymer. Non-limiting examples for an insoluble polymer that can be used for forming the controlled membrane film 150 include a cellulose ester, a cellulose diester, a cellulose triester, a cellulose ether, a cellulose ester-ether, cellulose acylate, cellulose diacylate, cellulose triacylate, cellulose acetate, cellulose diacetate, cellulose triacetate, cellulose acetate propionate, or cellulose acetate butyrate, etc. Other suitable polymers are described in U.S. Pat. Nos. 3,845,770, 3,916,899, 4,008, 719, 4,036,228 and 411,210 which are incorporated herein by reference. For example, one membrane material as such can be cellulose acetate CA-398-10, which comprises an acetyl content of 39.3%-40.3% and is commercially available from Eastman Fine Chemicals.

Herein optionally, the controlled membrane film 150 can comprise at least one insoluble polymer and at least one soluble excipient (i.e. pore-forming agent) which are mixed together with one another. The at least one soluble excipient may optionally include at least one pore-forming agent and or at least one plasticizer. The major compositions in the controlled membrane film 150 and their ratios are summarized in Table 1.

TABLE 1

| Main ingredients in the controlled membrane film of the oral dosage. | | |
| --- | --- | --- |
| INGREDINT | Preferred | More Preferred |
| Polymer | 50-99% | 75-95% |
| Pore-forming agent | 0-40% | 2-20% |
| Plasticizer | 0-25% or 0-30% | 0-15% |

Optionally, the controlled membrane film 150 can comprise one or more insoluble polymers as described above and at least one pore-forming agent. The at least one pore-forming agent increases the volume of fluid (water and biological fluid) penetrating into the core to enable the dosage form of the pharmaceutical composition to dispense substantially all of the antihyperglycemic drug through the passageway and/or the porous membrane. The pore-forming agent can be a water-soluble material or an enteric material. Some examples of the preferred materials that are useful as pore-forming agent include sodium chloride, potassium chloride, sucrose, sorbitol, mannitol, polyethylene glycol (PEG), propylene glycol, hydroxypropyl cellulose, hydroxypropyl methylcellulose, hydroxypropyl methylcellulose phthalate, cellulose acetate phthalate, polyvinyl alcohols, methacrylic acid copolymers and mixtures thereof. The preferred pore-forming agent is PEG 400, PEG 3350, PEG 6000, and PEG 8000. The pore-forming agent comprises approximately 0 to about 40% of the total weight of the coating, most preferably about 2% to about 20% of the total weight of the coating. The pore-forming agent dissolves or leaches from the membrane film to form paths in the membrane film for the fluid to enter the core and dissolve the active ingredient. The pore-forming agent may also be a drug that is water soluble such as metformin or its pharmaceutically acceptable salts or a drug that is soluble under intestinal conditions. If the pore-forming agent is a drug, the present dosage form has the added advantage of providing an immediate release of the drug which is selected as the pore-forming agent.

Optionally yet preferably, the controlled membrane film 150 may also be formed with certain excipients such as a plasticizer. Some commonly known plasticizers include adipate, azelate, enzoate, citrate, stearate, isoebucate, sebacate, triethyl citrate, tri-n-butyl citrate, acetyl tri-n-butyl citrate, citric acid esters, and those described in the Encyclopedia of Polymer Science and Technology, Vol. 10 (1969), published by John Wiley & Sons. The preferred plasticizers are triacetin, acetylated monoglyceride, grape seed oil, olive oil, sesame oil, acetyltributylcitrate, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, and the like. Depending on the particular plasticizer, amounts of from 0 to about 25%, and preferably about 2% to about 15% of the plasticizer can be used based upon the total weight of the coating.

As used herein, the term "passageway" can refer to an opening (e.g. an aperture, orifice, bore, hole, or alike) of the controlled membrane film 150 allowing the release of the at least one antidiabetic agent that is encapsulated in the core portion 100 therethrough, and can also refer to a weakened region or an erodible region (e.g. an erodible plug that erodes in an aqueous environment) in the controlled membrane film 150 which can be induced to form an opening therein to thereby allow release of the at least one antidiabetic agent therethrough. A detailed description of a "passageway" can be found in U.S. Pat. Nos. such as U.S. Pat. Nos. 3,845,770, 3,916,899, 4,034,758, 4,063,064, 4,077, 407, 4,088,864, 4,783,337, and 5,071,607, the disclosures of which are hereby incorporate by reference. In certain embodiments, the passageways of the controlled membrane film 150 in the oral dosage form 001 are formed by mechanical or laser drilling. In other embodiments, the passageways are formed by making an indentation onto the core prior to the membrane coating to form a weakened area of the membrane at the point of the indentation.

Optionally, the oral dosage form of the pharmaceutical composition can further comprise an inner seal film (not shown in FIG. 1), which is sandwiched between the core portion 100 and the controlled membrane film 150. The inner seal film substantially encapsulates the core portion 100, and is configured to provide a sealing means therefor before the core portion 100 is coated with the controlled membrane film 150 so that the characteristics of the active pharmaceutical ingredients included in the core portion of the oral dosage form of the pharmaceutical composition provided in the present disclosure is not influenced during the coating process.

Herein, the inner seal film can comprise at least one film-forming polymer and one or more excipients that are pharmaceutically acceptable. Examples of a film-forming polymer include hydroxypropyl methylcellulose (HPMC), hydroxypropylcellulose (HPC), sodium carboxymethylcellulose, polyvinylpyrrolidone (PVP), polyvinyl alcohol, polyethylene glycol (PEG), hypromellose, or other suitable water-soluble polymer materials. The excipients contained in the outer seal film can similarly include plasticizer(s), pigment(s) (i.e. dye(s) or colorant(s)), dispersing agent(s), and antioxidant(s). The compositions of the plasticizers, pigments, dispersing agents and the antioxidants are known to people killed in the field. Examples of a plasticizer include polyethylene glycol grades 400 to 3350 and triethyl citrate. An example of a dispersing agent can be hydrated aluminum silicate (Kaolin). Examples of an antioxidant include α-tocopherol, γ-tocopherol, δ-tocopherol, extracts of natural origin rich in tocopherol, L-ascorbic acid and its sodium or calcium salts, ascorbyl palmitate, propyl gallate, octyl gallate, dodecyl gallate, butylated hydroxytoluene (BHT), or butylated hydroxyanisole (BHA), etc. The preferred antioxidant is propyl gallate. Herein the antioxidant serves to prevent oxidative degradation of the core portion of the oral dosage form of the pharmaceutical composition provided in the present disclosure.

Herein, the relative amount of the inner seal film relative to the entire tablet, can vary within the scope of the invention and depend on the desirable drug load, which can range from about 0.5%-40%, and preferably from 2% to 10%, of the tablet dosage form by weight.

According to certain embodiments, the at least one first antidiabetic agent in the core portion 100 of the oral dosage form 001 of the pharmaceutical composition comprises a biguanide or a pharmaceutically acceptable salt thereof. According to some embodiments of the oral dosage form, the biguanide can be metformin, and further optionally, the at least one first antidiabetic agent in the core portion 100 of the oral dosage form consists of metformin hydrochloride, which can have a dosage of 500-1000 mg. As such, with this substantial osmotic pump formulation provided by the oral dosage form provided herein, the biguanide or a pharmaceutically acceptable salt thereof can realize a controlled or sustained release after a subject takes the oral dosage form, yet without employing any expanding polymer.

In certain embodiments, the core portion of the controlled release oral dosage form of metformin hydrochloride in the present invention further comprises, besides the at least one antidiabetic agent (i.e. antihyperglycemic drug or active drug, e.g. metformin hydrochloride), optionally at least one binding agent (also known as "binder"), and/or optionally at least one absorption enhancer, and/or optionally at least one lubricant, as listed in Table 2.

TABLE 2

| Main ingredients (active drug and excipients) in the core portion of the oral dosage. | | |
|---|---|---|
| INGREDINT | Preferred | More Preferred |
| Antidiabetic agent(s) | 50-98% | 75-95% |
| Binder(s) | 0-40% | 3-15% |
| Absorption Enhancer(s) | 0-20% | 2-10% |
| Lubricant(s) | 0-10% | 1-3% |

Herein, a binding agent may be any conventionally known pharmaceutically acceptable binder such as polyvinyl pyrrolidone (also known as "providone" or "polyvidone", shorted as "PVP"), hydroxypropyl cellulose, hydroxyethyl cellulose, ethylcellulose, polymethacrylate, waxes and the like. Mixtures of the aforementioned binding agents may also be used. The preferred binding agents are water soluble such as polyvinyl pyrrolidone having a weight average molecular weight of 25,000 to 3,000,000. The binding agent can constitute approximately about 0 to about 40%, preferably about 3% to about 15%, of the total weight of the core portion of the oral dosage form.

The core portion may optionally comprise an absorption enhancer. The absorption enhancer can be any type of absorption enhancer commonly known in the art such as a fatty acid, a surfactant, a chelating agent, a bile salt or mixtures thereof. Examples of some preferred absorption enhancers are fatty acids such as capric acid, oleic acid and their monoglycerides, surfactants such as sodium lauryl sulfate, sodium taurocholate and polysorbate 80, chelating agents such as citric acid, phytic acid, ethylenediamine tetraacetic acid (EDTA) and ethylene glycol-big (B-amino-ethyl ether-N,N,N,N-tetraacetic acid (EGTA)). The core portion can comprise approximately 0 to about 20% of the absorption enhancer based on the total weight of the core portion, and most preferably about 2% to about 10% of the total weight of the core portion.

A lubricant that can be used in the core portion of the oral dosage form provided herein can be any type of lubricants commonly known in the art such as magnesium stearate, stearic acid, sodium fumarate, glyceryl behenate, etc. and most preferably about 0.2% to about 2% of the total weight of the core portion.

In addition to the abovementioned binder(s), absorption enhancer(s) and lubricant(s), other excipients that may optionally be included into the core portion of the oral dosage form can include pigments or dyes.

In one specific embodiment of the oral dosage form, the core tablet (i.e. the core portion) can comprise metformin hydrochloride (i.e. active drug), Povidone (polyvinyl pyrrolidone, or PVP), USP (United State Pharmacopeia) grade (i.e. binder), sodium lauryl (i.e. absorption enhancer), and magnesium stearate (i.e. lubricant).

According to certain embodiments, metformin hydrochloride can obtain peak plasma levels from 7.5 to 15 hours after administration under various conditions. Additionally, the controlled release of metformin can effectively reduce the gastrointestinal (GI) side effects (e.g. diarrhea, nausea, and vomiting, etc.) that are frequently caused by the agent. Based on FIGS. 3 and 4 for the plasma concentration figures of Controlled Release metformin/sitagliptin tablets at fasting and fed conditions, it achieves such effect to have the peak plasma levels between 7.5-15 hours.

In embodiments where the at least one first antidiabetic agent in the core portion 100 is metformin or a pharmaceutically acceptable salt thereof, the controlled release oral dosage form provides a mean maximum plasma concentration ($C_{max}$) of the drug that is about 700-1500 ng/ml, and preferably about 900-1250 ng/ml, based on administration of a controlled release oral dosage form providing 1000 mg/100 mg once-a-day dose of metformin/sitagliptin.

In embodiments where the at least one first antidiabetic agent in the core portion 100 is metformin or a pharmaceutically acceptable salt thereof, the controlled release dosage form provides a mean $AUC_{0-24\ hr}$ that is about 7000-16000 ng·hr/ml, and preferably about 9000-14000 ng·hr/ml, based on administration of a controlled release oral dosage form providing 1000 mg/100 mg once-a-day dose of metformin/sitagliptin.

Because of the above configuration, for the controlled-release dosage form of the pharmaceutical composition comprising a biguanide (e.g., metformin) that is suitable for once-a-day administration to human subjects with non-insulin-dependent diabetes mellitus (NIDDM) or prediabetes, the dosage form can control blood glucose levels for up to about 24 hours and can provide controlled release of the drug with a mean time to maximum plasma concentration ($T_{max}$) of the drug from 7.5 to 15 hours after administration and a width at 50% of the height of a mean plasma concentration/time curve of the drug from about 6-15 hours.

According to some embodiments, the at least one first antidiabetic agent in the core portion 100 may, in addition to the biguanide or a pharmaceutically acceptable salt thereof, further comprises one or more other types of antidiabetic agents, which can also realize a controlled release from the oral dosage form after the oral administration, because of the controlled membrane film 150 in the oral dosage form of the pharmaceutical composition.

According to some other embodiments, the at least one first antidiabetic agent in the core portion 100 may comprise no biguanide but comprise one or more other types of antidiabetic agents, which can realize a controlled release from the oral dosage form after the oral administration.

According to certain embodiments of the oral dosage form 001 of the pharmaceutical composition provided herein, the at least one second antidiabetic agent in the outer portion 200 can comprise at least one of a DPP-4 inhibitor (e.g. sitagliptin, saxagliptin, linagliptin, or alogliptin, etc.), a sulfonylurea (e.g. glipizide, or glyburide, etc.), a meglitinide (e.g. repaglinide, nateglinide, or mitiglinide, etc.), a thiazolidinedione (e.g. pioglitazone, or rosiglitazone, etc.), a SGLT2 inhibitor (e.g. canagliflozin, ertugliflozin, empagliflozin, or dapagliflozin, etc.), or an alpha-glucosidase inhibitor. In the oral dosage form of the pharmaceutical composition provided herein, because the at least one second antidiabetic agent residing in the outer portion 200 of the oral dosage form is substantially coated on the outer surface of the controlled membrane film 150, which is further released immediately after a the oral dosage form is taken, thus the at least one second antidiabetic agent has little influence on the controlled release of the at least one first antidiabetic agent (e.g. metformin HCl) from the core portion 100 of the oral dosage form.

In the oral dosage form of the pharmaceutical composition provided herein, each of the at least one second antidiabetic agent can be configured to have a dosage and a formulation that correspondingly matches with a dosage and formulation of the at least one first antidiabetic agent (e.g. metformin) to thereby realize a complementary and synergistic effect. For example, the dosage and formulation of each of the at least one second antidiabetic agent can be configured based on the dosage and formulation of metformin and on the PK/PD profile of the each of the at least one second antidiabetic agent.

In one specific embodiment, the oral dosage form of the pharmaceutical composition comprises an extended-release form of metformin having a dosage of approximately 500-1000 mg and an immediate-release form of the DPP-4 inhibitor sitagliptin having a dosage of approximately 25-100 mg, which reside in the core portion 100 and the outer portion 200 of the oral dosage form, respectively.

In another specific embodiment, the oral dosage form of the pharmaceutical composition comprises a controlled-release form of metformin having a dosage of approximately 500-1000 mg and an immediate-release form of the SGLT-2 inhibitor dapagliflozin having a dosage of approximately 2.5-10 mg, which reside in the core portion 100 and the outer portion 200 of the oral dosage form, respectively.

According to certain embodiments of the oral dosage form of the pharmaceutical composition provided herein, an outer seal film 250 is arranged to coat an outside surface of the outer portion 200 as also illustrated in FIG. 1. The outer seal film 250 is configured to provide a protective coating for the oral dosage form, so that the characteristics of the active pharmaceutical ingredients included in the oral dosage form are not influenced by the environment.

Herein, the outer seal film 250 of the oral dosage form can have similar compositions as the inner seal film described above. Briefly, the outer seal film can comprise at least one pharmaceutically acceptable film-forming polymer and one or more pharmaceutically acceptable excipients.

Examples of a film-forming polymer include hydroxypropyl methylcellulose (HPMC), hydroxypropylcellulose (HPC), sodium carboxymethylcellulose, polyvinylpyrrolidone (PVP), polyvinyl alcohol, polyethylene glycol (PEG), hypromellose, or other suitable water-soluble polymer materials. A particular form of HPMC for use as a film-forming polymer is HPMC 2910.

The excipients contained in the outer seal film can similarly include plasticizer(s), pigment(s) (i.e. dye(s) or colorant(s)), dispersing agent(s), and antioxidant(s). Examples of a plasticizer include polyethylene glycol grades 400 to 3350 and triethyl citrate. An example of a dispersing agent can be hydrated aluminum silicate (Kaolin). Examples of an antioxidant include α-tocopherol, γ-tocopherol, δ-tocopherol, extracts of natural origin rich in tocopherol, L-ascorbic acid and its sodium or calcium salts, ascorbyl palmitate, propyl gallate, octyl gallate, dodecyl gallate, butylated hydroxytoluene (BHT), or butylated hydroxyanisole (BHA), etc. The preferred antioxidant is propyl gallate. Herein the antioxidant serves to prevent oxidative degradation of the core portion of the oral dosage form of the pharmaceutical composition provided in the present disclosure.

Herein, the relative amount of the outer seal film relative to the entire tablet, can vary within the scope of the invention and depend on the desirable drug load, which can range from about 0.5%-40%, and preferably from 2% to 10%, of the tablet dosage form by weight.

Herein, the relative amount of film-forming polymer(s) and plasticizer may vary within the scope of the invention.

The plasticizer maybe used independently or as a combination in various ratio. The relative amount of the plasticizer relative to the entire tablet, can vary within the scope of the invention and depend on the desirable drug load. In most cases, the plasticizer can constitute from about 0.1% to 10% by weight of the tablet dosage form, preferably from 1% to 8%. Additionally, the level of antioxidant can constitute from about 0.03% to 0.05%. If hydrated aluminum silicate is used as the dispersing agent, it can constitute from about 0.2% to 5% by weight of the tablet dosage form, preferably from 0.5% to 2%.

The following examples further describe and demonstrate embodiments within the scope of the present invention. These embodiments are given solely for the purpose of illustration and are not intended to be construed as limitations of the present invention as many variations thereof are possible without departing from the spirit and scope of the invention.

According to some preferred embodiments, the oral dosage form of the pharmaceutical composition comprises a fixed-dose combination of a controlled-release form of metformin or a pharmaceutically acceptable salt thereof and an immediate-release form of the sitagliptin or a pharmaceutically acceptable salt thereof. Herein, more specifically metformin or a pharmaceutically acceptable salt thereof corresponds to the at least one first antidiabetic agent arranged at the core portion 100 of the oral dosage form 001 as illustrated in FIG. 1, and sitagliptin or a pharmaceutically acceptable salt thereof corresponds to the second antidiabetic agent arranged at the outer portion 200 of the oral dosage form 001 as illustrated in FIG. 1. In these embodiments of the oral dosage form, these above two antidiabetic agents are substantially formulated into dosage forms suitable for the simultaneous administration.

One particular solid dosage form as such relates to tablets comprising a fixed-dose combination of a controlled-release form of metformin hydrochloride coated with an immediate-release form of sitagliptin phosphate. Optionally, the unit dosage strength of the metformin hydrochloride for incorporation into the fixed-dose combination of the present disclosure can be 500, 750 or 1000 milligrams. Further optionally, the unit dosage strength of sitagliptin free base anhydrate (active moiety) for inclusion into the fixed-dose combination pharmaceutical compositions of the present disclosure can be 25, 50, or 100 milligrams. An equivalent amount of sitagliptin phosphate monohydrate to the sitagliptin free base anhydrate used in the pharmaceutical compositions can correspondingly be 32.125, 64.25 or 128.5 milligrams.

According to some other embodiments, the oral dosage form of the pharmaceutical composition comprises a fixed-dose combination of a controlled-release form of metformin or a pharmaceutically acceptable salt thereof and an immediate-release form of an SGLT-2 inhibitor (e.g. dapagliflozin) or a pharmaceutically acceptable salt thereof. One particular solid dosage form as such relates to tablets comprising a fixed-dose combination of a controlled-release form of metformin hydrochloride coated with an immediate-release form dapagliflozin. Optionally, the unit dosage strength of the metformin hydrochloride for incorporation into the fixed-dose combination of the present disclosure can be 500, 750 or 1000 milligrams, and the unit dosage strength of the dapagliflozin for incorporation into the fixed-dose combination of the present disclosure can be 2.5-10 mg.

According to yet some other embodiments, the oral dosage form of the pharmaceutical composition comprises a fixed-dose combination of a controlled-release form of metformin or a pharmaceutically acceptable salt thereof and an immediate-release form of a sulfonylurea (e.g. glipizide or glyburide) or a pharmaceutically acceptable salt thereof, such as glipizide or glyburide, and the unit dosage strength of the glipizide or glyburide for incorporation into the fixed dosage combination of the present disclosure can be 1.25-10 mg.

According to yet some other embodiments, the oral dosage form of the pharmaceutical composition comprises a fixed-dose combination of a controlled-release form of metformin or a pharmaceutically acceptable salt thereof and an immediate-release form of a meglitinide (e.g. repaglinide or nateoglinide) or a pharmaceutically acceptable salt thereof, such as repaglinide or nateoglinide, and the unit dosage strength of the repaglinide for incorporation into the fixed dosage combination of the present disclosure can be 0.5-5 mg; and the unit dosage strength of the nateoglinide for incorporation into the fixed dosage combination of the present disclosure can be 30-60 mg.

According to yet some other embodiments, the oral dosage form of the pharmaceutical composition comprises a fixed-dose combination of a controlled-release form of metformin or a pharmaceutically acceptable salt thereof and an immediate-release form of a thiazolidinedione (e.g. pioglitazone or rosiglitazone) or a pharmaceutically acceptable salt thereof. Herein, the unit dosage strength of the pioglitazone for incorporation into the fixed dosage combination of the present disclosure can be 15-45 mg, while the unit dosage strength of the rosiglitazone for incorporation into the fixed dosage combination of the present disclosure can be 1-4 mg.

According to yet some other embodiments, the oral dosage form of the pharmaceutical composition comprises a fixed-dose combination of a controlled-release form of metformin or a pharmaceutically acceptable salt thereof and an immediate-release form of an alpha-glucosidase inhibitor (e.g. acarbose or miglitol) or a pharmaceutically acceptable salt thereof. For example, the unit dosage strength of the acarbose for incorporation into the fixed dosage combination of the present disclosure can be 12.5-100 mg, while the unit dosage strength of the miglitol for incorporation into the fixed dosage combination of the present disclosure can be 12.5-100 mg.

The following examples further describe and demonstrate embodiments within the scope of the present invention. These embodiments are given solely for the purpose of illustration and are not intended to be construed as limitations of the present disclosure as many variations thereof are possible without departing from the spirit and scope of the invention.

Embodiment 1

This embodiment illustrates the preparation of an oral dosage form of the pharmaceutical composition, which substantially comprises an osmatic pump controlled release metformin hydrochloride (HCl) core tablet (i.e. core portion, 1000 mg composition) coated with an immediate-release (IR) sitagliptin phosphate film (i.e. outer portion, 100 mg composition).

To be more specific, the cores of the controlled release metformin HCl membrane coated tablets were formulated by a fluid bed granulation, where hydroxypropyl cellulose (HPC-EF) was dissolved into water to make approximately 5% solids w/w HPC-EF solution, which was then sprayed on delumped metformin HCl, sorbitol and sodium lauryl sulfate.

The dried granules were dried and milled through a co-mill 0.8 mm. Milled granules were blended with magnesium stearate for approximately 5 minutes at 25 RPM in a V-Blender. The granulation conditions for the core portions of the oral dosage form, i.e. metformin core tablets (shown as "metformin CR (controlled release)") are summarized in Table 3.

TABLE 3

Metformin ER Granulation Conditions

| | |
|---|---|
| Granulation Temperature (° C.) | 45-55 |
| Air Volume (HZ) | 25-45 |
| Atomization Air Pressure (Bar) | 2-3 |
| Fluid Bed Spray Rate (g/min) | 5-10 |

Note:
The LOD % of the granules after drying was NMT 3% as determine by moisture balance., where the term LOD is short for "Loss On Dry", and the term NMT for "No More Than".

The final blend was compressed on an automatic tablet press into tablets using 10.0×20.5 mm long tooling.

The core tablets were then coated with a controlled membrane film by coating with a solution comprising CA-398-10 (i.e. polymer material for the controlled membrane film) and PEG 6000 (i.e. flux enhancer for the controlled membrane film) in acetone solution, followed by curing for 60 minutes at 50° C. The controlled membrane coating condition is summarized in Table 4.

TABLE 4

Controlled Membrane Coating Conditions.

| | |
|---|---|
| Product Temperature (° C.) | 15-30 |
| Air Volume (HZ) | 35 |
| Atomization Air Pressure (Bar) | 0.9 |
| Spray Rate (g/min) | 10-20 |
| Pan Speed (rpm) | 17-18 |
| Inlet Temperature (° C.) | 20-30 |

The coated tablets were laser drilled two holes (e.g. one hole on each side of the tablet, as illustrated in FIG. 1), and each hole should be within ±5 mm of the middle of the tablet, the diameter of orifice should be between 0.40 to 0.60 mm, and the depth of orifice should be between 0.10 to 2.00 mm.

The sitagliptin phosphate coating solution was prepared by mixing all the excipients and sitagliptin phosphate in the required amount of purified water using a suitable homogenizer until the solids were dissolved. The sitagliptin phosphate coating solution was prepared to a total of approximately 18.0% solids w/w, which was then applied onto the metformin coated tablets and the amount of solids deposited in the active pharmaceutical ingredient ("API") film layer (i.e. the outer portion of the oral dosage) was controlled to achieve the desired sitagliptin dose.

The membrane-coated metformin HCl controlled release core tablets were loaded into a suitable perforated side-vented coating pan with baffles fitted with single spray guns to produce a spray fan to cover the entire width of the tablet bed; the average weight of warmed uncoated tablet was determined as the initial starting weight; the sitagliptin phosphate coating suspension was sprayed onto the tablet bed at a suitable spray rate and atomization pressure; spraying with the sitagliptin phosphate coating suspension was continued while monitoring the tablet weight until the required weight gain was obtained; an approximate dried coat weight of 130 mg equivalent to 50 mg sitagliptin (as free base) or 260 mg equivalent to 100 mg of sitagliptin (as free base) was deposited over the tablet cores; spraying was stopped, and the tablets were dried and discharged from the coating pan. The sitagliptin film coating conditions are summarized in Table 5.

TABLE 5

Sitagliptin Film Coating Conditions

| | |
|---|---|
| Product Temperature (° C.) | 35-45 |
| Air Volume (HZ) | 35/45 |
| Atomization Air Pressure (Bar) | 1.0 |
| Spray Rate (g/min) | 9-10 |
| Pan Speed (rpm) | 15 |
| Inlet Temperature (° C.) | 55-65 |

The Sitagliptin coated tablets were then coated with a seal coating solution, which is made of hypromellose and polyethylene glycol an Opadry material or other suitable water-soluble material by first dissolving the hypromellose and polyethylene glycol, preferably Opadry Clear (YS-1-7006) which is a mixture coating material with hypromellose and polyethylene glycol, in purified water. The Opadry coating solution was then sprayed onto the core tablets using a pan coater under the following conditions: exhaust air temperature of 38-42° C.; atomization pressure of 28-40 psi; and spray rate of 10-15 ml/min. The Opadry Clear of the coating constitutes about 20-25 mg/tablet.

In the oral dosage form (i.e. Metformin HCl controlled release core tablet (1000 mg) coated with immediate release sitagliptin phosphate outer film (100 mg)) obtained by the preparation method (i.e. EMBODIMENT 1) as described above, the various compositions for the core portion (i.e. metformin HCl controlled release tablet, 1000 mg composition) and for the outer portion (i.e. the sitagliptin phosphate film, 100 mg composition) are summarized in Table 6 and Table 7, respectively.

TABLE 6

Metformin HCl Controlled Release Tablet, 1000 mg Composition.

| Materials | % w/w |
|---|---|
| Metformin HCl | 83.3 |
| Sodium Lauryl Sulfate. | 3.8 |
| Sorbitol | 5.2 |
| HPC EF | 5.1 |
| Magnesium Stearate | 0.8 |
| Cellulose Acetate | 1.7 |
| Polyethylene glycol | 0.25 |
| Total | 100.0 |

TABLE 7

Sitagliptin Phosphate Film, 100 mg Composition.

| Materials | % w/w |
|---|---|
| Sitagliptin Phosphate (100 mg Free base) | 52.05 |
| HPMC E5 | 47.95 |
| Total | 100.0 |

Embodiment 2

This embodiment illustrates the preparation of an oral dosage form of the pharmaceutical composition, which substantially comprises an osmatic pump controlled release metformin hydrochloride (HCl) core tablet (i.e. core portion, 1000 mg composition) coated with an immediate-release (IR) sitagliptin phosphate film (i.e. outer portion, 100 mg composition).

To be more specific, the cores of the controlled release metformin HCl membrane coated tablets were formulated by a fluid bed granulation, where povidone (PVP-K90) was dissolved into water to make approximately 7% solids w/w PVP solution, which was then sprayed on delumped metformin HCl and sodium lauryl sulfate.

The dried granules were dried and milled through a co-mill 0.8 mm. Milled granules were blended with magnesium stearate for approximately 5 minutes at 25 RPM in a V-Blender. The granulation conditions for the core portions of the oral dosage form, i.e. metformin core tablets (shown as "metformin CR (controlled release)") are summarized in Table 8.

TABLE 8

| Metformin ER Granulation Conditions | |
| --- | --- |
| Granulation Temperature (° C.) | 33-45 |
| Air Volume (HZ) | 25-45 |
| Atomization Air Pressure (Bar) | 2-2.5 |
| Fluid Bed Spray Rate (g/min) | 5-10 |

Note:
The LOD % of the granules after drying was NMT 3% as determine by moisture balance., where the term LOD is short for "Loss On Dry", and the term NMT for "No More Than".

The final blend was compressed on an automatic tablet press into tablets using 12.0×12.0 mm round tooling for the 500 mg formulation and 10.0×20.5 mm long or 10.3×21.2 mm oval tooling for the 1000 mg formulation. The core tablets (i.e. the core portion of the oral dosage form) obtained thereby were then coated with a seal coating solution, which is made of hypromellose and polyethylene glycol or other suitable water-soluble material by first dissolving the hypromellose and polyethylene glycol, preferably Opadry Clear (YS-1-7006) which is a mixture coating material with hypromellose and polyethylene glycol, in purified water. The coating solution was then sprayed onto the core tablets using a pan coater under the following conditions: exhaust air temperature of 38-42° C.; atomization pressure of 28-40 psi; and spray rate of 10-15 ml/min. The Opadry Clear of the coating constitutes about 10-15 mg/tablet.

The seal film coated tablets were then coated with a controlled membrane film by coating with a solution comprising CA-398-10 (i.e. polymer material for the controlled membrane film) and PEG 3350 (i.e. pore forming agent/plasticizing agent for the controlled membrane film) in acetone solution, followed by curing for 60 minutes at 50° C. The controlled membrane coating condition is summarized in Table 9.

TABLE 9

| Controlled Membrane Coating Conditions. | |
| --- | --- |
| Product Temperature (° C.) | 18.4-24.8 |
| Air Volume (HZ) | 35 |
| Atomization Air Pressure (Bar) | 0.9 |
| Spray Rate (g/min) | 14.4-15.9 |
| Pan Speed (rpm) | 17-18 |
| Inlet Temperature (° C.) | 24.3-30 |

The coated tablets were laser drilled two holes (e.g. one hole on each side of the tablet, as illustrated in FIG. 1), and each hole should be within ±5 mm of the middle of the tablet, the diameter of orifice should be between 0.30 to 0.80 mm, and the depth of orifice should be between 0.10 to 2.00 mm.

The sitagliptin phosphate coating solution was prepared by mixing all the excipients and sitagliptin phosphate in the required amount of purified water using a suitable homogenizer until the solids were dissolved. The sitagliptin phosphate coating solution was prepared to a total of approximately 18.0% solids w/w, which was then applied onto the metformin coated tablets and the amount of solids deposited in the active pharmaceutical ingredient ("API") film layer (i.e. the outer portion of the oral dosage) was controlled to achieve the desired sitagliptin dose.

The membrane-coated metformin HCl controlled release core tablets were loaded into a suitable perforated side-vented coating pan with baffles fitted with single spray guns to produce a spray fan to cover the entire width of the tablet bed; the average weight of warmed uncoated tablet was determined as the initial starting weight; the sitagliptin phosphate coating suspension was sprayed onto the tablet bed at a suitable spray rate and atomization pressure; spraying with the sitagliptin phosphate coating suspension was continued while monitoring the tablet weight until the required weight gain was obtained; an approximate dried coat weight of 130 mg equivalent to 50 mg sitagliptin (as free base) or 260 mg equivalent to 100 mg of sitagliptin (as free base) was deposited over the tablet cores; spraying was stopped, and the tablets were dried and discharged from the coating pan. The sitagliptin film coating conditions are summarized in Table 10.

TABLE 10

| Sitagliptin Film Coating Conditions | |
| --- | --- |
| Product Temperature (° C.) | 37.4-45.0 |
| Air Volume (HZ) | 35/45 |
| Atomization Air Pressure (Bar) | 1.0 |
| Spray Rate (g/min) | 9-10 |
| Pan Speed (rpm) | 15 |
| Inlet Temperature (° C.) | 58.6-65.6 |

The Sitagliptin coated tablets were then coated with a seal coating solution, which is made of hypromellose and polyethylene glycol an Opadry material or other suitable water-soluble material by first dissolving the hypromellose and polyethylene glycol, preferably Opadry Clear (YS-1-7006) which is a mixture coating material with hypromellose and polyethylene glycol, in purified water. The Opadry coating solution was then sprayed onto the core tablets using a pan coater under the following conditions: exhaust air temperature of 38-42° C.; atomization pressure of 28-40 psi; and spray rate of 10-15 ml/min. The Opadry Clear of the coating constitutes about 20-25 mg/tablet.

In the oral dosage form (i.e. Metformin HCl controlled release core tablet (1000 mg) coated with immediate release sitagliptin phosphate outer film (100 mg)) obtained by the preparation method (i.e. EMBODIMENT 2) as described above, the various compositions for the core portion (i.e. metformin HCl controlled release tablet, 1000 mg composition) and for the outer portion (i.e. the sitagliptin phosphate film, 100 mg composition) are summarized in Table 11 and Table 12, respectively.

TABLE 11

Metformin HCl Controlled Release Tablet, 1000 mg Composition.

| Materials | % w/w |
| --- | --- |
| Metformin HCl | 84.7 |
| Sodium Lauryl Sulfate. | 4.2 |
| Povidone K90 | 6.8 |
| Magnesium Stearate | 0.4 |
| Hypromellose | 1.4 |
| Polyethylene glycol | 0.6 |
| Cellulose Acetate | 1.7 |
| Polyethylene glycol | 0.2 |
| Total | 100.0 |

TABLE 12

Sitagliptin Phosphate Film, 100 mg Composition.

| Materials | % w/w |
| --- | --- |
| Sitagliptin Phosphate (100 mg Free base) | 52.05 |
| HPMC E5 | 47.95 |
| Total | 100.0 |

Embodiment 3

This embodiment illustrates the preparation of osmatic pump controlled-release (CR) metformin HCl core tablet (1000 mg composition) coated with an immediate-release (IR) sitagliptin phosphate film (50 mg composition).

The procedures used were similar to, and can therefore reference to, EMBODIMENT 2 as described above, with certain variations. More specifically, the metformin CR granulation conditions, the controlled membrane coating conditions, and the sitagliptin film coating conditions are summarized in Table 13, Table 14, and Table 15, respectively.

TABLE 13

Metformin CR Granulation Conditions.

| Granulation Temperature (° C.) | 33-45 |
| --- | --- |
| Air Volume (HZ) | 25-45 |
| Atomization Air Pressure (Bar) | 2-2.5 |
| Fluid Bed Spray Rate (g/min) | 5-10 |

Note:
The LOD % of the granules after drying was NMT 3% as determine by moisture balance., where the term LOD is short for "Loss On Dry", and the term NMT for "No More Than".

TABLE 14

Controlled Membrane Coating Conditions.

| Product Temperature (° C.) | 18.4-24.8 |
| --- | --- |
| Air Volume (HZ) | 35 |
| Atomization Air Pressure (Bar) | 0.9 |
| Spray Rate (g/min) | 14.4-15.9 |
| Pan Speed (rpm) | 17-18 |
| Inlet Temperature (° C.) | 24.3-30 |

TABLE 15

Sitagliptin Film Coating Conditions.

| Product Temperature (° C.) | 37.6-42.0 |
| --- | --- |
| Air Volume (HZ) | 25/40 |
| Atomization Air Pressure (Bar) | 1.0 |
| Spray Rate (g/min) | 7-8.8 |
| Pan Speed (rpm) | 15 |
| Inlet Temperature (° C.) | 64.4-65.2 |

In the oral dosage form (i.e. Metformin HCl controlled release core tablet (1000 mg) coated with immediate release sitagliptin phosphate outer film (50 mg)) obtained by the preparation method (i.e. EMBODIMENT 3) as described above, the various compositions for the core portion (i.e. metformin HCl controlled release tablet, 1000 mg composition) and for the outer portion (i.e. the sitagliptin phosphate film, 50 mg composition) are summarized in Table 16 and Table 17, respectively.

TABLE 16

Metformin HCl ER Tablet, 1000 mg Composition.

| Materials | % w/w |
| --- | --- |
| Metformin HCl | 84.7 |
| Sodium Lauryl Sulfate. | 4.2 |
| Povidone K90 | 6.8 |
| Magnesium Stearate | 0.4 |
| Hypromellose | 1.4 |
| Polyethylene glycol | 0.6 |
| Cellulose Acetate | 1.7 |
| Polyethylene glycol | 0.2 |
| Total | 100.0 |

TABLE 17

Sitagliptin Phosphate Film, 50 mg Composition.

| Materials | % w/w |
| --- | --- |
| Sitagliptin Phosphate (50 mg Free base) | 52.05 |
| HPMC E5 | 47.95 |
| Total | 100.0 |

Embodiment 4

This embodiment illustrates the preparation of osmatic pump controlled-release (CR) metformin HCl tablet (500 mg composition) coated with an immediate-release (IR) sitagliptin phosphate film (50 mg composition).

The procedures used were similar to, and can therefore reference to, EMBODIMENT 2 as described above, with certain variations. More specifically, the metformin CR granulation conditions, the controlled membrane coating conditions, and the sitagliptin film coating conditions are summarized in Table 18, Table 19, and Table 20, respectively.

TABLE 18

| Metformin CR Granulation Conditions. | |
|---|---|
| Granulation Temperature (° C.) | 33.7-45.4 |
| Air Volume (HZ) | 25-35 |
| Atomization Air Pressure (Bar) | 2-2.5 |
| Fluid Bed Spray Rate (g/min) | 7.54 |

Note:
The LOD % of the granules after drying was NMT 3% as determine by moisture balance., where the term LOD is short for "Loss On Dry", and the term NMT for "No More Than".

TABLE 19

| Controlled Membrane Coating Conditions. | |
|---|---|
| Product Temperature (° C.) | 17.8-23.4 |
| Air Volume (HZ) | 35 |
| Atomization Air Pressure (Bar) | 0.9 |
| Spray Rate (g/min) | 14.5 |
| Pan Speed (rpm) | 19 |
| Inlet Temperature (° C.) | 22.1-38.0 |

TABLE 20

| Sitagliptin Film Coating Conditions. | |
|---|---|
| Product Temperature (° C.) | 36.8-46.5 |
| Air Volume (HZ) | 35/43 |
| Atomization Air Pressure (Bar) | 0.9 |
| Spray Rate (g/min) | 9.51 |
| Pan Speed (rpm) | 15 |
| Inlet Temperature (° C.) | 64.6-65.9 |

In the oral dosage form (i.e. Metformin HCl controlled release core tablet (500 mg) coated with immediate release sitagliptin phosphate outer film (50 mg)) obtained by the preparation method (i.e. EMBODIMENT 4) as described above, the various compositions for the core portion (i.e. metformin HCl controlled release tablet, 500 mg composition) and for the outer portion (i.e. the sitagliptin phosphate film, 50 mg composition) are summarized in Table 21 and Table 22, respectively.

TABLE 21

| Metformin HCl CR Tablet, 500 mg Composition. | |
|---|---|
| Materials | % w/w |
| Metformin HCl | 82.5 |
| Sodium Lauryl Sulfate. | 4.1 |
| Povidone K90 | 6.6 |
| Magnesium Stearate | 0.4 |
| Hypromellose | 1.3 |
| Polyethylene glycol | 0.6 |
| Cellulose Acetate | 4.0 |
| Polyethylene glycol | 0.5 |
| Total | 100.0 |

TABLE 22

| Sitagliptin Phosphate Film, 50 mg Composition. | |
|---|---|
| Materials | % w/w |
| Sitagliptin Phosphate (50 mg Free base) | 52.05 |
| HPMC E5 | 47.95 |
| Total | 100.0 |

Embodiment 5

This embodiment illustrates the preparation of osmatic pump controlled-release (CR) metformin HCl tablet (1000 mg composition) coated with an immediate-release (IR) Sitagliptin phosphate film (100 mg composition).

The procedures used were similar to, and can therefore reference to, EMBODIMENT 1 as described above, with certain variations. More specifically, the metformin CR granulation conditions, the controlled membrane coating conditions, and the sitagliptin phosphate film coating conditions are summarized in Table 23, Table 24, and Table 25, respectively.

TABLE 23

| Metformin CR Granulation Conditions. | |
|---|---|
| Granulation Temperature (° C.) | 33-45 |
| Air Volume (HZ) | 25-45 |
| Atomization Air Pressure (Bar) | 2-2.5 |
| Fluid Bed Spray Rate (g/min) | 5-10 |

Note:
The LOD % of the granules after drying was NMT 3% as determine by moisture balance., where the term LOD is short for "Loss On Dry", and the term NMT for "No More Than".

TABLE 24

| Controlled Membrane Coating Conditions. | |
|---|---|
| Product Temperature (° C.) | 18.4-24.8 |
| Air Volume (HZ) | 35 |
| Atomization Air Pressure (Bar) | 0.9 |
| Spray Rate (g/min) | 14.4-15.9 |
| Pan Speed (rpm) | 17-18 |
| Inlet Temperature (° C.) | 24.3-30 |

TABLE 25

| Sitagliptin Film Coating Conditions. | |
|---|---|
| Product Temperature (° C.) | 39.2-49.2 |
| Air Volume (HZ) | 25/40 |
| Atomization Air Pressure (Bar) | 1.0 |
| Spray Rate (g/min) | 4.64 |
| Pan Speed (rpm) | 15 |
| Inlet Temperature (° C.) | 64.8-65.2 |

In the oral dosage form (i.e. Metformin HCl controlled release core tablet (1000 mg) coated with immediate release sitagliptin phosphate outer film (100 mg)) obtained by the preparation method (i.e. EMBODIMENT 5) as described above, the various compositions for the core portion (i.e. metformin HCl controlled release tablet, 1000 mg composition) and for the outer portion (i.e. the sitagliptin phosphate film, 100 mg composition) are summarized in Table 26 and Table 27, respectively.

TABLE 26

| Metformin HCl CR Tablet, 1000 mg Composition. | |
|---|---|
| Materials | % w/w |
| Metformin HCl | 84.7 |
| Sodium Lauryl Sulfate. | 4.2 |
| Povidone K90 | 6.8 |

TABLE 26-continued

| Metformin HCl CR Tablet, 1000 mg Composition. | |
| --- | --- |
| Materials | % w/w |
| Magnesium Stearate | 0.4 |
| Hypromellose | 1.4 |
| Polyethylene glycol | 0.6 |
| Cellulose Acetate | 1.7 |
| Polyethylene glycol | 0.2 |
| Total | 100.0 |

TABLE 27

| Sitagliptin Phosphate Film, 100 mg Composition. | |
| --- | --- |
| Materials | % w/w |
| Sitagliptin Phosphate (100 mg Free base) | 61.19 |
| HPMC E5 | 31.19 |
| PEG 3350 | 7.62 |
| Total | 100.0 |

Embodiment 6

This embodiment illustrates the preparation of osmatic pump controlled-release (CR) metformin HCl tablet (1000 mg composition) coated with an immediate-release (IR) sitagliptin phosphate film (100 mg composition).

The procedures used were similar to, and can therefore reference to, EMBODIMENT 1 as described above, with certain variations. More specifically, the metformin CR granulation conditions, the controlled membrane coating conditions, and the sitagliptin phosphate film coating conditions are summarized in Table 28, Table 29, and Table 30, respectively.

TABLE 28

| Metformin CR Granulation Conditions. | |
| --- | --- |
| Granulation Temperature (° C.) | 33-45 |
| Air Volume (HZ) | 25-45 |
| Atomization Air Pressure (Bar) | 2-2.5 |
| Fluid Bed Spray Rate (g/min) | 5-10 |

Note:
The LOD % of the granules after drying was NMT 3% as determine by moisture balance., where the term LOD is short for "Loss On Dry", and the term NMT for "No More Than".

TABLE 29

| Controlled Membrane Coating Conditions | |
| --- | --- |
| Product Temperature (° C.) | 18.4-24.8 |
| Air Volume (HZ) | 35 |
| Atomization Air Pressure (Bar) | 0.9 |
| Spray Rate (g/min) | 14.4-15.9 |
| Pan Speed (rpm) | 17-18 |
| Inlet Temperature (° C.) | 24.3-30 |

TABLE 30

| Sitagliptin Film Coating Conditions | |
| --- | --- |
| Product Temperature (° C.) | 40.8-47.4 |
| Air Volume (rpm) | 25/40 HZ |

TABLE 30-continued

| Sitagliptin Film Coating Conditions | |
| --- | --- |
| Atomization Air Pressure (Bar) | 1.2 |
| Spray Rate (g/min) | 2.82-5.20 |
| Pan Speed (rpm) | 19 |
| Inlet Temperature (° C.) | 64.8-68.0 |

In the oral dosage form (i.e. Metformin HCl controlled release core tablet (1000 mg) coated with immediate release sitagliptin phosphate outer film (100 mg)) obtained by the preparation method (i.e. EMBODIMENT 6) as described above, the various compositions for the core portion (i.e. metformin HCl controlled release tablet, 1000 mg composition) and for the outer portion (i.e. the sitagliptin phosphate film, 100 mg composition) are summarized in Table 31 and Table 32, respectively.

TABLE 31

| Metformin HCl CR Tablet, 1000 mg Composition | |
| --- | --- |
| Materials | % w/w |
| Metformin HCl | 84.7 |
| Sodium Lauryl Sulfate. | 4.2 |
| Povidone K90 | 6.8 |
| Magnesium Stearate | 0.4 |
| Hypromellose | 1.4 |
| Polyethylene glycol | 0.6 |
| Cellulose Acetate | 1.7 |
| Polyethylene glycol | 0.2 |
| Total | 100.0 |

TABLE 32

| Sitagliptin Phosphate Film, 100 mg Composition | |
| --- | --- |
| Materials | % w/w |
| Sitagliptin Phosphate (100 mg Free base) | 61.19 |
| Povidone K90 | 20.24 |
| PEG 3350 | 18.57 |
| Total | 100.0 |

Embodiment 7

This embodiment illustrates the preparation of osmatic pump controlled-release (CR) metformin HCl tablet (1000 mg composition) coated with an immediate-release (IR) sitagliptin phosphate film (100 mg composition).

The procedures used were similar to, and can therefore reference to, EMBODIMENT 1 as described above, with certain variations. More specifically, the metformin CR granulation conditions, the controlled membrane coating conditions, and the sitagliptin phosphate film coating conditions are summarized in Table 33, Table 34, and Table 35, respectively.

TABLE 33

| Metformin CR Granulation Conditions. | |
| --- | --- |
| Granulation Temperature (° C.) | 33-45 |
| Air Volume (HZ) | 25-45 |

TABLE 33-continued

| Metformin CR Granulation Conditions. | |
| --- | --- |
| Atomization Air Pressure (Bar) | 2-2.25 |
| Fluid Bed spray Rate (g/min) | 5-10 |

Note:

The LOD % of the granules after drying was NMT 3% as determine by moisture balance., where the term LOD is short for "Loss On Dry", and the term NMT for "No More Than".

TABLE 34

| Controlled Membrane Coating Conditions | |
| --- | --- |
| Product Temperature (° C.) | 18.4-24.8 |
| Air Volume (HZ) | 35 |
| Atomization Air Pressure (Bar) | 0.9 |
| Spray Rate (g/min) | 14.4-15.9 |
| Pan Speed (rpm) | 17-18 |
| Inlet Temperature (° C.) | 24.3-30 |

TABLE 35

| Sitagliptin Film Coating Conditions | |
| --- | --- |
| Product Temperature (° C.) | 40.8-47.4 |
| Air Volume (rpm) | 25/40 HZ |
| Atomization Air Pressure (Bar) | 1.2 |
| Spray Rate (g/min) | 2.82-5.20 |
| Pan Speed (rpm) | 19 |
| Inlet Temperature (° C.) | 64.8-68.0 |

In the oral dosage form (i.e. Metformin HCl controlled release core tablet (1000 mg) coated with immediate release sitagliptin phosphate outer film (100 mg)) obtained by the preparation method (i.e. EMBODIMENT 7) as described above, the various compositions for the core portion (i.e. metformin HCl controlled release tablet, 1000 mg composition) and for the outer portion (i.e. the sitagliptin phosphate film, 100 mg composition) are summarized in Table 36 and Table 37, respectively.

TABLE 36

| Metformin HCl CR Tablet, 1000 mg Composition | |
| --- | --- |
| Materials | % w/w |
| Metformin HCl | 82.2 |
| Sodium Lauryl Sulfate. | 4.11 |
| Povidone K90 | 6.58 |
| Magnesium Stearate | 4.89 |
| Cellulose Acetate | 1.98 |
| Polyethylene glycol | 0.24 |
| Total | 100.0 |

TABLE 37

| Sitagliptin Phosphate Film, 100 mg Composition | |
| --- | --- |
| Materials | % w/w |
| Sitagliptin Phosphate (100 mg Free base) | 66.67 |
| Hydroxypropyl Cullulose | 33.34 |
| Total | 100.0 |

Embodiment 8

This embodiment illustrates the preparation of osmatic pump controlled-release (CR) metformin HCl tablet (500 mg composition) coated with an immediate-release (IR) sitagliptin phosphate film (50 mg composition).

The procedures used were similar to, and can therefore reference to, EMBODIMENT 1 as described above, with certain variations. More specifically, the metformin CR granulation conditions, the controlled membrane coating conditions, and the sitagliptin phosphate film coating conditions are summarized in Table 38, Table 39, and Table 40, respectively.

TABLE 38

| Metformin CR Granulation Conditions. | |
| --- | --- |
| Granulation Temperature (° C.) | 33-45 |
| Air Volume (HZ) | 25-45 |
| Atomization Air Pressure (Bar) | 2-2.25 |
| Fluid Bed spray Rate (g/min) | 5-10 |

Note:

The LOD % of the granules after drying was NMT 3% as determine by moisture balance., where the term LOD is short for "Loss On Dry", and the term NMT for "No More Than".

TABLE 39

| Controlled Membrane Coating Conditions | |
| --- | --- |
| Product Temperature (° C.) | 18.4-24.8 |
| Air Volume (HZ) | 35 |
| Atomization Air Pressure (Bar) | 0.9 |
| Spray Rate (g/min) | 14.4-15.9 |
| Pan Speed (rpm) | 17-18 |
| Inlet Temperature (° C.) | 24.3-30 |

TABLE 40

| Sitagliptin Film Coating Conditions | |
| --- | --- |
| Product Temperature (° C.) | 40.8-47.4 |
| Air Volume (rpm) | 25/40 HZ |
| Atomization Air Pressure (Bar) | 1.2 |
| Spray Rate (g/min) | 2.82-5.20 |
| Pan Speed (rpm) | 19 |
| Inlet Temperature (° C.) | 64.8-68.0 |

In the oral dosage form (i.e. Metformin HCl controlled release core tablet (500 mg) coated with immediate release sitagliptin phosphate outer film (50 mg)) obtained by the preparation method (i.e. EMBODIMENT 8) as described above, the various compositions for the core portion (i.e. metformin HCl controlled release tablet, 500 mg composition) and for the outer portion (i.e. the sitagliptin phosphate film, 50 mg composition) are summarized in Table 41 and Table 42, respectively.

TABLE 41

| Metformin HCl CR Tablet, 500 mg Composition | |
| --- | --- |
| Materials | % w/w |
| Metformin HCl | 80.55 |
| Sodium Lauryl Sulfate. | 6.44 |
| Povidone K90 | 4.03 |

TABLE 41-continued

| Metformin HCl CR Tablet, 500 mg Composition | |
| --- | --- |
| Materials | % w/w |
| Magnesium Stearate | 4.79 |
| Cellulose Acetate | 3.74 |
| Polyethylene glycol | 0.45 |
| Total | 100.0 |

TABLE 42

| Sitagliptin Phosphate Film, 50 mg Composition | |
| --- | --- |
| Materials | % w/w |
| Sitagliptin Phosphate (50 mg Free base) | 66.67 |
| Hydroxypropyl Cullulose | 33.34 |
| Total | 100.0 |

Embodiment 9

This embodiment illustrates the preparation of osmatic pump controlled-release (CR) metformin HCl tablet (750 mg composition) coated with an immediate-release (IR) sitagliptin phosphate film (50 mg composition).

The procedures used were similar to, and can therefore reference to, EMBODIMENT 1 as described above, with certain variations. More specifically, the metformin CR granulation conditions, the controlled membrane coating conditions, and the sitagliptin phosphate film coating conditions are summarized in Table 43, Table 44, and Table 45, respectively.

TABLE 43

| Metformin CR Granulation Conditions. | |
| --- | --- |
| Granulation Temperature (° C.) | 33-45 |
| Air Volume (HZ) | 25-45 |
| Atomization Air Pressure (Bar) | 2-2.25 |
| Fluid Bed spray Rate (g/min) | 5-10 |

Note:
The LOD % of the granules after drying was NMT 3% as determine by moisture balance., where the term LOD is short for "Loss On Dry", and the term NMT for "No More Than".

TABLE 44

| Controlled Membrane Coating Conditions | |
| --- | --- |
| Product Temperature (° C.) | 18.4-24.8 |
| Air Volume (HZ) | 35 |
| Atomization Air Pressure (Bar) | 0.9 |
| Spray Rate (g/min) | 14.4-15.9 |
| Pan Speed (rpm) | 17-18 |
| Inlet Temperature (° C.) | 24.3-30 |

TABLE 45

| Sitagliptin Film Coating Conditions | |
| --- | --- |
| Product Temperature (° C.) | 40.8-47.4 |
| Air Volume (rpm) | 25/40 HZ |
| Atomization Air Pressure (Bar) | 1.2 |

TABLE 45-continued

| Sitagliptin Film Coating Conditions | |
| --- | --- |
| Spray Rate (g/min) | 2.82-5.20 |
| Pan Speed (rpm) | 19 |
| Inlet Temperature (° C.) | 64.8-68.0 |

In the oral dosage form (i.e. Metformin HCl controlled release core tablet (750 mg) coated with immediate release sitagliptin phosphate outer film (50 mg)) obtained by the preparation method (i.e. EMBODIMENT 9) as described above, the various compositions for the core portion (i.e. metformin HCl controlled release tablet, 750 mg composition) and for the outer portion (i.e. the sitagliptin phosphate film, 50 mg composition) are summarized in Table 46 and Table 47, respectively.

TABLE 46

| Metformin HCl CR Tablet, 750 mg Composition | |
| --- | --- |
| Materials | % w/w |
| Metformin HCl | 81.29 |
| Sodium Lauryl Sulfate. | 6.50 |
| Povidone K90 | 4.06 |
| Magnesium Stearate | 4.84 |
| Cellulose Acetate | 2.95 |
| Polyethylene glycol | 0.35 |
| Total | 100.0 |

TABLE 47

| Sitagliptin Phosphate Film, 50 mg Composition | |
| --- | --- |
| Materials | % w/w |
| Sitagliptin Phosphate (50 mg Free base) | 66.67 |
| Hydroxypropyl Cellulose | 33.34 |
| Total | 100.0 |

Embodiment 10

This embodiment illustrates the preparation of osmatic pump controlled-release (CR) metformin HCl tablet (750 mg composition) coated with an immediate-release (IR) sitagliptin phosphate film (100 mg composition).

The procedures used were similar to, and can therefore reference to, EMBODIMENT 1 as described above, with certain variations. More specifically, the metformin CR granulation conditions, the controlled membrane coating conditions, and the sitagliptin phosphate film coating conditions are summarized in Table 48, Table 49, and Table 50, respectively.

TABLE 48

| Metformin CR Granulation Conditions. | |
| --- | --- |
| Granulation Temperature (° C.) | 33-45 |
| Air Volume (HZ) | 25-45 |
| Atomization Air Pressure (Bar) | 2-2.5 |
| Fluid Bed Spray Rate (g/min) | 5-10 |

Note:
The LOD % of the granules after drying was NMT 3% as determine by moisture balance., where the term LOD is short for "Loss On Dry", and the term NMT for "No More Than".

TABLE 49

| Controlled Membrane Coating Conditions | |
| --- | --- |
| Product Temperature (° C.) | 18.4-24.8 |
| Air Volume (HZ) | 35 |
| Atomization Air Pressure (Bar) | 0.9 |
| Spray Rate (g/min) | 14.4-15.9 |
| Pan Speed (rpm) | 17-18 |
| Inlet Temperature (° C.) | 24.3-30 |

TABLE 50

| Sitagliptin Film Coating Conditions | |
| --- | --- |
| Product Temperature (° C.) | 40.8-47.4 |
| Air Volume (rpm) | 25/40 HZ |
| Atomization Air Pressure (Bar) | 1.2 |
| Spray Rate (g/min) | 2.82-5.20 |
| Pan Speed (rpm) | 19 |
| Inlet Temperature (° C.) | 64.8-68.0 |

In the oral dosage form (i.e. Metformin HCl controlled release core tablet (750 mg) coated with immediate release sitagliptin phosphate outer film (100 mg)) obtained by the preparation method (i.e. EMBODIMENT 10) as described above, the various compositions for the core portion (i.e. metformin HCl controlled release tablet, 750 mg composition) and for the outer portion (i.e. the sitagliptin phosphate film, 100 mg composition) are summarized in Table 51 and Table 52, respectively.

TABLE 51

| Metformin HCl CR Tablet, 750 mg Composition | |
| --- | --- |
| Materials | % w/w |
| Metformin HCl | 81.29 |
| Sodium Lauryl Sulfate. | 6.50 |
| Povidone K90 | 4.06 |
| Magnesium Stearate | 4.84 |
| Cellulose Acetate | 2.95 |
| Polyethylene glycol | 0.35 |
| Total | 100.0 |

TABLE 52

| Sitagliptin Phosphate Film, 100 mg Composition | |
| --- | --- |
| Materials | % w/w |
| Sitagliptin Phosphate (100 mg Free base) | 66.67 |
| Hydroxypropyl Cellulose | 33.34 |
| Total | 100.0 |

Embodiment 11

This embodiment illustrates the preparation of osmatic pump controlled-release (CR) metformin HCl tablet (1000 mg composition) coated with an immediate-release (IR) sitagliptin phosphate film (50 mg composition).

The procedures used were similar to, and can therefore reference to, EMBODIMENT 1 as described above, with certain variations. More specifically, the metformin CR granulation conditions, the controlled membrane coating conditions, and the sitagliptin phosphate film coating conditions are summarized in Table 53, Table 54, and Table 55, respectively.

TABLE 53

| Metformin CR Granulation Conditions. | |
| --- | --- |
| Granulation Temperature (° C.) | 33-45 |
| Air Volume (HZ) | 25-45 |
| Atomization Air Pressure (Bar) | 2-2.5 |
| Fluid Bed Spray Rate (g/min) | 5-10 |

Note:
The LOD % of the granules after drying was NMT 3% as determine by moisture balance., where the term LOD is short for "Loss On Dry", and the term NMT for "No More Than".

TABLE 54

| Controlled Membrane Coating Conditions | |
| --- | --- |
| Product Temperature (° C.) | 18.4-24.8 |
| Air Volume (HZ) | 35 |
| Atomization Air Pressure (Bar) | 0.9 |
| Spray Rate (g/min) | 14.4-15.9 |
| Pan Speed (rpm) | 17-18 |
| Inlet Temperature (° C.) | 24.3-30 |

TABLE 55

| Sitagliptin Film Coating Conditions | |
| --- | --- |
| Product Temperature (° C.) | 40.8-47.4 |
| Air Volume (rpm) | 25/40 HZ |
| Atomization Air Pressure (Bar) | 1.2 |
| Spray Rate (g/min) | 2.82-5.20 |
| Pan Speed (rpm) | 19 |
| Inlet Temperature (° C.) | 64.8-68.0 |

In the oral dosage form (i.e. Metformin HCl controlled release core tablet (1000 mg) coated with immediate release sitagliptin phosphate outer film (50 mg)) obtained by the preparation method (i.e. EMBODIMENT 11) as described above, the various compositions for the core portion (i.e. metformin HCl controlled release tablet, 1000 mg composition) and for the outer portion (i.e. the sitagliptin phosphate film, 50 mg composition) are summarized in Table 56 and Table 57, respectively.

TABLE 56

| Metformin HCl CR Tablet, 1000 mg Composition | |
| --- | --- |
| Materials | % w/w |
| Metformin HCl | 82.20 |
| Sodium Lauryl Sulfate. | 6.58 |
| Povidone K90 | 4.11 |
| Magnesium Stearate | 4.89 |
| Cellulose Acetate | 1.98 |
| Polyethylene glycol | 0.24 |
| Total | 100.0 |

TABLE 57

| Sitagliptin Phosphate Film, 50 mg Composition | |
| --- | --- |
| Materials | % w/w |
| Sitagliptin Phosphate (100 mg Free base) | 66.67 |
| Hydroxypropyl Cellulose | 33.34 |
| Total | 100.0 |

In the following, the in vitro dissolution profiles for metformin HCl and sitagliptin phosphate and the in vivo plasma bioavailability for metformin of certain embodiments of the oral dosage form of the antidiabetic pharmaceutical compositions are examined.

Figure 2A:
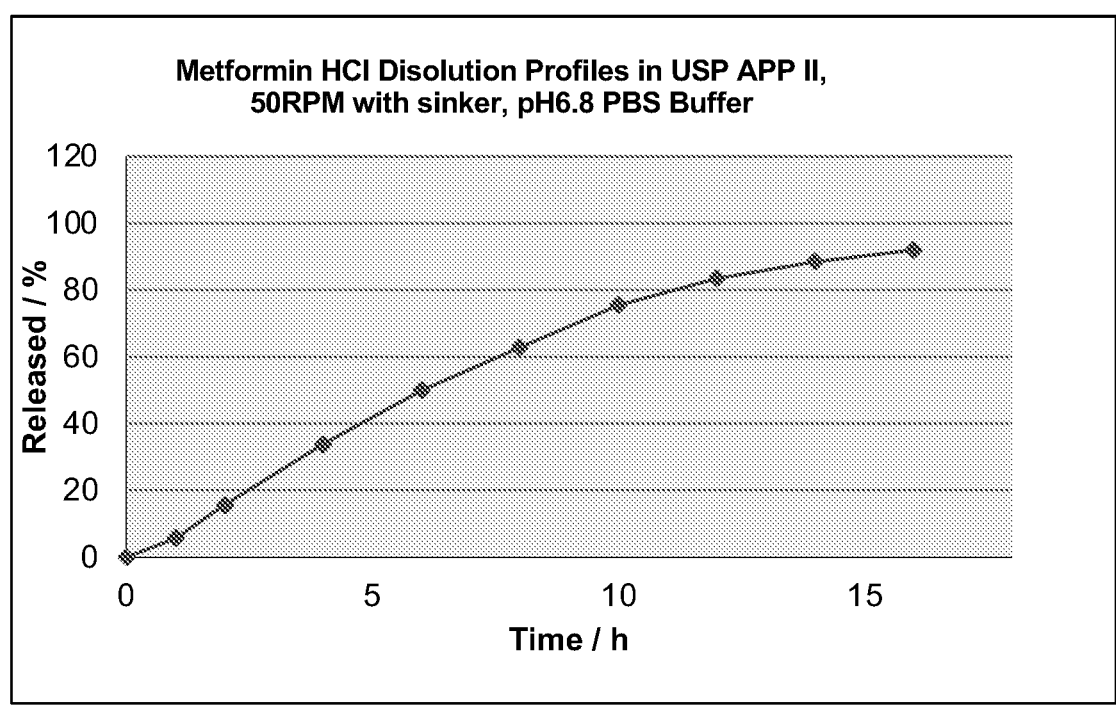
FIGS. 2A and 2B respectively show the dissolution profiles of metformin HCl and sitagliptin phosphate of a sample oral dosage form (i.e. Metformin HCl/Sitagliptin phosphate CR 1000/100 mg tablets formulation provided in Embodiment 1 of this present disclosure)
Figure 2B:
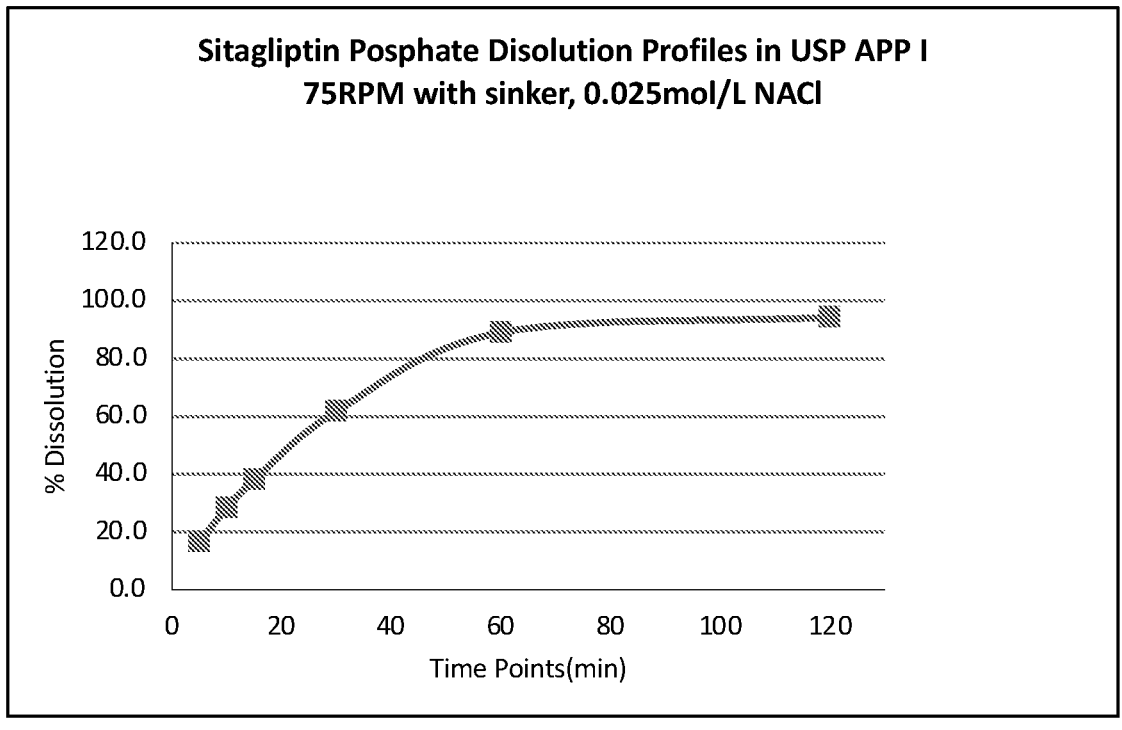

FIGS. 2A and 2B respectively show the in vitro dissolution profiles of metformin HCl and sitagliptin phosphate in the Metformin HCl/Sitagliptin phosphate CR 1000/100 mg tablets formulation provided in Embodiment 1 of this present disclosure. The in vitro dissolution test of the Metformin HCl was performed in a pH 6.8 buffer, as measured by USP Apparatus Type II at 50 rpm at 37° C., and the in vitro dissolution test of the sitagliptin phosphate was performed in a 0.025 mol/mL sodium chloride solution, as measured by USP Apparatus Type I at 75 rpm at 37° C. As shown in FIG. 2B, sitagliptin phosphate dissolves very quickly in the NaCl solution, with 29% dissolved at approximately 10 min, and almost fully dissolved after 60 min, thereby realizing an immediate release in the oral dosage form. As further shown in FIG. 2A, metformin HCl dissolves much slower compared with sitagliptin phosphate, with 14-40% dissolved at approximately 4 hr, 32-85% dissolved at approximately 8 hr, and almost fully dissolved after approximately 24 hr.

Furthermore, the in vitro dissolution profiles for metformin HCl and sitagliptin phosphate in each of the above mentioned embodiments of the oral dosage form of the pharmaceutical composition are respectively determined and further compared with the dissolution profile of certain known antidiabetic prescription medicines (Janumet XR 1000 mg, Fortamet 500 mg, and Fortamet 1000 mg) as references.

Herein Janumet XR is the brand name for sitagliptin phosphate and metformin hydrochloride extended-release tablets, which is an antidiabetic prescription medicine that contains sitagliptin phosphate (JANUVIA®) and extended-release metformin HCl. Fortamet is the brand name for metformin HCl tablets, which is an antidiabetic prescription medicine that contains either 500 mg or 1000 mg metformin HCl.

The dissolution profiles are determined under the following conditions:

Dissolution Medium: 900 ml, United State Pharmacopeia Phosphate buffer pH 6.8, refer United State Pharmacopeia for the detail procedures of preparation.

Dissolution Method: United State Pharmacopeia Dissolution Test Device Type 1 Apparatus (Basket method), 100 rpm at 37° C.

Detection Method: the High Performance Liquid Chromatography method is developed and used to measure the dissolved Metformin HCl and Sitagliptin Phosphate in the collected samples in the tested time points.

The following tables (i.e. Table 58 and Table 59) respectively shows the dissolution results for sitagliptin phosphate and metformin HCl in the first six embodiments of the oral dosage form described above (i.e. Embodiments 1-6) and in the three known antidiabetic prescription medicines (Janumet XR 1000 mg, Fortamet 500 mg, and Fortamet 1000 mg).

TABLE 58

Sitagliptin Phosphate Dissolution Results for Embodiments 1-6.

| Time (min) | EMBODIMENT 1 (100 mg) * | EMBODIMENT 2 (100 mg) * | EMBODIMENT 3 (50 mg) * | EMBODIMENT 4 (50 mg) * | EMBODIMENT 5 (100 mg) * | EMBODIMENT 6 (100 mg) * | Janumet XR 1000 mg |
|---|---|---|---|---|---|---|---|
| 10 | 29 | 28 | 60 | 39 | 32 | 64 | 26 |
| 15 | 39 | 38 | 78 | 51 | 49 | 90 | 55 |
| 30 | 64 | 62 | 98 | 73 | 92 | 97 | 81 |
| 60 | 91 | 89 | 100 | 96 | 103 | 98 | 96 |

Note:

* the free base weight of sitagliptin phosphate

TABLE 59

Metformin HCl CR Tablets Dissolution Results for Embodiments 1-6.

| Time (hrs) | EMBODIMENT 1 (1000 mg) | EMBODIMENT 2 (1000 mg) | EMBODIMENT 3 (1000 mg) | EMBODIMENT 4 (500 mg) | EMBODIMENT 5 (1000 mg) | EMBODIMENT 6 (1000 mg) | Janumet XR 1000 mg | Fortamet 500 mg | Fortamet 1000 mg |
|---|---|---|---|---|---|---|---|---|---|
| 1 | 6 | 6 | 13 | 4 | 5 | 12 | 25 | 7 | 8 |
| 2 | 16 | 19 | 27 | 16 | 23 | 25 | 46 | 19 | 18 |
| 4 | 34 | 41 | 54 | 31 | 50 | 55 | 68 | 36 | 38 |
| 6 | 50 | N/A | 81 | 55 | N/A | N/A | 83 | 51 | 66 |
| 8 | 63 | 75 | 92 | 75 | 73 | 84 | 94 | 73 | 85 |
| 10 | 75 | N/A | 97 | 96 | N/A | N/A | 101 | 86 | 91 |
| 12 | 84 | 90 | 99 | 99 | 92 | 93 | 104 | 94 | 96 |
| 16 | 92 | 98 | 101 | 99 | 96 | 96 | 104 | 99 | 99 |

The following tables (i.e. Table 60 and Table 61) respectively shows the dissolution results for sitagliptin phosphate and metformin HCl in the second five embodiments of the oral dosage form described above (i.e. Embodiments 7-11) and in the three known antidiabetic prescription medicines (Janumet XR 1000 mg, Fortamet 500 mg, and Fortamet 1000 mg).

TABLE 60

Sitagliptin Phosphate Dissolution Results for Embodiments 7-11.

| Time (min) | EMBODIMENT 7 (100 mg) * | EMBODIMENT 8 (50 mg) * | EMBODIMENT 9 (50 mg) * | EMBODIMENT 10 (100 mg) * | EMBODIMENT 11 (50 mg) * | Janumet XR 1000 mg |
|---|---|---|---|---|---|---|
| 10 | 29 | 33 | 33 | 30 | 28 | 26 |
| 15 | 48 | 56 | 56 | 48 | 51 | 55 |
| 30 | 84 | 88 | 88 | 84 | 87 | 81 |
| 60 | 97 | 92 | 95 | 99 | 93 | 96 |

Note:
* the free base weight of sitagliptin phosphate

TABLE 61

Metformin HCI CR Tablets Dissolution Results for Embodiments 7-11.

| Time (hrs) | EMBODIMENT 7 (1000 mg) | EMBODIMENT 8 (500 mg) | EMBODIMENT 9 (750 mg) | EMBODIMENT 10 (750 mg) | EMBODIMENT 11 (1000 mg) | Janumet XR 1000 mg | Fortamet 500 mg | Fortamet 1000 mg |
|---|---|---|---|---|---|---|---|---|
| 1 | 1 | 1 | 1 | 1 | 2 | 25 | 7 | 8 |
| 2 | 7 | 6 | 5 | 8 | 7 | 46 | 19 | 18 |
| 4 | 19 | 17 | 14 | 23 | 18 | 68 | 36 | 38 |
| 6 | 30 | 28 | 23 | 36 | 28 | 83 | 51 | 66 |
| 8 | 40 | 39 | 32 | 47 | 37 | 94 | 73 | 85 |
| 10 | 49 | 49 | 40 | 57 | 48 | 101 | 86 | 91 |
| 12 | 58 | 59 | 48 | 66 | 56 | 104 | 94 | 96 |
| 16 | 72 | 75 | 62 | 77 | 68 | 104 | 99 | 99 |
| 20 | 83 | 86 | 74 | 89 | 76 | | | |
| 24 | 89 | 91 | 81 | 93 | 81 | | | |

The in vivo plasma bioavailability for metformin of one embodiment (Metformin HCl/Sitagliptin phosphate CR 1000/100 mg tablets formulation provided in Embodiment 1 of this present disclosure, i.e., "test formulation") of the oral dosage form of the antidiabetic pharmaceutical compositions in subjects under fasting or fed conditions is also examined and compared with the in vivo plasma bioavailability of one known antidiabetic prescription medicine (Fortamet 1000 mg, i.e., "reference formulation"), which is used as reference control.

Specifically, the plasma concentration of metformin provided in EMBODIMENT 1 (formulation T) and the known antidiabetic prescription medicine (formulation R) was determined at different time points (0, 2.0, 3.0, 4.0, 4.5, 5.0, 5.5, 6.0, 6.5, 7.0, 7.5, 8.0, 8.5, 9.0, 9.5, 10.0, 10.5, 11.0, 11.5, 12.0, 14.0, 16.0, 16.0, 20.0, 24.0, 28.0 and 36.0 hours) after the oral dosage form is orally administered to several subjects. The metformin plasma concentration results under fasting condition are summarized in Table 62 and Table 63, respectively.

It is noted that the plasma concentration of metformin is in the unit of ng/ml; each of the highlighted values (i.e. values in bold and underlined font) in the two tables indicates the maximum plasma concentration ($T_{max}$) of metformin for each subject after oral administration of a single dose of the oral dosage form of formulation T or formulation R; and the time point 0 represents the predose concentration of metformin.

TABLE 62

Plasma concentration (ng/ml) profiles of the metformin determined at different time points after a single dose of the reference formulation is orally administered to different subjects under fasting condition.

| Time | Subject ID No. | | | | | | | | | | | | CV |
|---|---|---|---|---|---|---|---|---|---|---|---|---|---|
| (hr) | 2 | 4 | 6 | 7 | 8 | 9 | 10 | 11 | 12 | 13 | 14 | Mean | % |
| 0 | 0.0 | 0.0 | 0.0 | 0.0 | 0.0 | 0.0 | 0.0 | 0.0 | 0.0 | 0.0 | 0.0 | 0.0 | — |
| 2.0 | 88.7 | 231.3 | 142.7 | 65.2 | 43.4 | 106.4 | 92.0 | 64.7 | 36.3 | 94.0 | 63.3 | 93.5 | 58.5 |
| 3.0 | 254.0 | 220.7 | 309.6 | 146.0 | 136.3 | 286.2 | 117.1 | 193.2 | 81.6 | 216.7 | 175.7 | 194.3 | 36.8 |
| 4.0 | 445.0 | 242.3 | 589.9 | 179.7 | 215.0 | 333.7 | 224.4 | 476.6 | 129.3 | 354.2 | 271.4 | 314.7 | 44.8 |
| 4.5 | 393.1 | 254.4 | 934.5 | 203.7 | 350.1 | 470.4 | 227.1 | 591.8 | 145.2 | 470.6 | 312.3 | 395.7 | 56.3 |
| 5.0 | 428.2 | 364.4 | 1222.5 | 211.5 | 437.6 | 640.3 | 242.4 | 709.2 | 154.7 | 1064.2 | 300.3 | 525.0 | 66.9 |
| 5.5 | 413.4 | 355.0 | 1473.6 | 263.7 | 441.0 | 715.3 | 234.6 | 732.5 | 209.0 | 1063.1 | 379.5 | 571.0 | 69.3 |
| 6.0 | 599.1 | 407.1 | 1742.1 | 292.6 | 477.3 | 702.8 | 259.1 | 752.2 | 215.9 | 1309.4 | 404.7 | 651.1 | 73.0 |
| 6.5 | 781.8 | 481.4 | 1647.4 | 334.3 | 574.2 | 734.0 | 324.9 | 840.5 | 277.0 | 1496.6 | 486.0 | 725.3 | 63.4 |
| 7.0 | 793.3 | 540.9 | 1713.5 | 333.6 | 626.0 | 731.5 | 378.1 | 1018.2 | 318.1 | 1612.0 | 508.1 | 779.4 | 62.2 |
| 7.5 | 966.5 | 574.1 | 1687.3 | 384.3 | 635.5 | 834.0 | 415.7 | 1106.8 | 561.7 | 1623.1 | 624.0 | 855.7 | 52.8 |
| 8.0 | 943.5 | 608.7 | 1482.2 | 512.1 | 697.6 | 841.2 | 489.7 | 1167.1 | 683.7 | 1555.8 | 650.0 | 875.6 | 42.6 |
| 8.5 | 1088.7 | 642.4 | 1479.4 | 557.1 | 724.2 | 785.5 | 516.3 | 1276.4 | 741.7 | 1383.5 | 725.2 | 901.9 | 38.1 |
| 9.0 | 1070.0 | 584.1 | 1354.2 | 588.5 | 679.1 | 763.4 | 484.2 | 1331.2 | 700.6 | 1251.2 | 781.8 | 871.7 | 36.8 |
| 9.5 | 1021.5 | 559.3 | 1267.3 | 598.0 | 772.1 | 813.7 | 468.3 | 1227.5 | 833.2 | 1158.0 | 821.0 | 867.3 | 31.4 |
| 10.0 | 1168.7 | 585.5 | 1106.7 | 720.5 | 752.8 | 807.7 | 527.7 | 1174.8 | 827.6 | 1246.8 | 881.1 | 890.9 | 27.8 |
| 10.5 | 1199.8 | 643.0 | 1118.9 | 989.0 | 803.0 | 859.0 | 522.7 | 1214.6 | 845.7 | 1247.9 | 940.2 | 944.0 | 25.3 |
| 11.0 | 1235.8 | 689.8 | 911.2 | 1137.8 | 750.3 | 895.4 | 565.9 | 1279.5 | 846.3 | 1244.2 | 1055.0 | 964.7 | 25.2 |
| 11.5 | 1257.6 | 866.8 | 861.8 | 1161.4 | 769.6 | 972.0 | 596.6 | 1252.5 | 827.3 | 1151.6 | 1097.5 | 983.1 | 22.0 |
| 12.0 | 1275.7 | 886.4 | 811.5 | 1282.6 | 775.4 | 897.9 | 587.1 | 1222.9 | 752.2 | 1093.1 | 1180.9 | 978.7 | 24.7 |
| 14.0 | 1183.2 | 627.1 | 484.5 | 1343.0 | 646.9 | 547.0 | 646.0 | 616.9 | 492.0 | 603.6 | 912.3 | 736.6 | 38.8 |
| 16.0 | 911.3 | 377.3 | 302.2 | 1118.5 | 548.9 | 446.1 | 626.8 | 337.6 | 402.5 | 371.0 | 634.4 | 552.4 | 46.8 |
| 20.0 | 402.9 | 166.4 | 146.6 | 686.9 | 346.8 | 188.8 | 692.1 | 202.2 | 180.0 | 186.3 | 421.0 | 329.1 | 61.7 |
| 24.0 | 164.5 | 86.6 | 81.0 | 281.7 | 240.0 | 71.6 | 442.7 | 88.0 | 119.6 | 89.7 | 189.8 | 168.6 | 68.2 |
| 28.0 | 69.2 | 43.2 | 36.3 | 133.5 | 108.9 | 37.0 | 209.0 | 44.2 | 103.4 | 58.4 | 76.7 | 83.6 | 63.0 |
| 36.0 | 0.0 | 21.1 | 0.0 | 29.1 | 22.7 | 0.0 | 46.9 | 0.0 | 29.6 | 29.0 | 28.8 | 18.8 | 86.5 |

TABLE 63

Plasma concentration (ng/ml) profiles of the metformin determined at different time points after a single dose of the test formulation is orally administered to different subjects under fasting condition.

| Time | Subject ID No. | | | | | | | | | | | | CV |
|---|---|---|---|---|---|---|---|---|---|---|---|---|---|
| (hr) | 2 | 4 | 6 | 7 | 8 | 9 | 10 | 11 | 12 | 13 | 14 | Mean | % |
| 0 | 0.0 | 0.0 | 0.0 | 0.0 | 0.0 | 0.0 | 0.0 | 0.0 | 0.0 | 0.0 | 0.0 | 0.0 | — |
| 2.0 | 132.3 | 143.0 | 127.0 | 83.5 | 87.0 | 82.9 | 105.1 | 93.4 | 52.4 | 89.7 | 103.4 | 100.0 | 26.1 |
| 3.0 | 310.2 | 227.7 | 237.4 | 119.0 | 166.0 | 182.3 | 185.7 | 234.3 | 101.1 | 175.5 | 208.2 | 195.2 | 29.8 |
| 4.0 | 429.4 | 222.4 | 331.0 | 169.6 | 226.2 | 212.0 | 236.9 | 330.7 | 162.8 | 270.6 | 412.1 | 273.1 | 33.4 |
| 4.5 | 460.0 | 193.2 | 369.5 | 185.9 | 265.6 | 244.7 | 301.1 | 355.5 | 183.1 | 327.2 | 374.2 | 296.4 | 30.6 |
| 5.0 | 633.4 | 197.4 | 417.8 | 214.7 | 327.9 | 305.8 | 348.1 | 372.0 | 274.4 | 489.0 | 342.6 | 356.6 | 34.8 |
| 5.5 | 769.6 | 241.8 | 512.3 | 290.2 | 353.8 | 325.6 | 503.7 | 478.5 | 273.1 | 668.0 | 373.4 | 435.4 | 38.8 |
| 6.0 | 844.7 | 273.9 | 588.8 | 377.0 | 390.9 | 383.3 | 537.2 | 513.9 | 306.9 | 800.2 | 446.0 | 496.6 | 37.7 |
| 6.5 | 872.2 | 271.4 | 733.3 | 475.8 | 413.1 | 449.3 | 639.7 | 563.7 | 480.2 | 890.6 | 479.4 | 569.9 | 34.2 |
| 7.0 | 933.6 | 290.3 | 838.0 | 487.4 | 391.7 | 488.1 | 670.0 | 630.5 | 604.6 | 882.3 | 580.9 | 617.9 | 33.0 |
| 7.5 | 895.6 | 309.9 | 907.3 | 537.5 | 410.9 | 462.1 | 725.3 | 789.2 | 716.1 | 817.1 | 635.6 | 655.2 | 30.7 |
| 8.0 | 938.1 | 340.2 | 922.0 | 597.6 | 430.4 | 507.4 | 744.4 | 990.0 | 692.4 | 917.4 | 701.1 | 707.4 | 31.3 |
| 8.5 | 983.4 | 354.4 | 1103.0 | 651.8 | 452.0 | 568.2 | 751.1 | 1075.0 | 782.8 | 662.7 | 746.4 | 739.2 | 32.6 |
| 9.0 | 920.7 | 367.9 | 1083.3 | 591.2 | 509.2 | 584.1 | 674.5 | 1034.8 | 1112.9 | 680.5 | 818.8 | 761.6 | 32.8 |
| 9.5 | 960.0 | 355.4 | 1152.4 | 648.7 | 510.6 | 587.4 | 723.6 | 1001.0 | 1152.1 | 663.7 | 885.6 | 785.5 | 33.5 |
| 10.0 | 905.4 | 422.3 | 1151.2 | 661.9 | 478.6 | 665.7 | 715.8 | 935.8 | 633.3 | 578.0 | 975.0 | 738.5 | 30.6 |
| 10.5 | 1033.8 | 547.9 | 1173.0 | 852.5 | 514.8 | 827.8 | 720.4 | 903.1 | 712.7 | 496.9 | 924.7 | 791.6 | 27.5 |
| 11.0 | 1153.0 | 543.0 | 1325.6 | 884.3 | 530.8 | 958.2 | 741.8 | 800.5 | 810.4 | 541.8 | 957.1 | 840.6 | 30.3 |
| 11.5 | 1044.4 | 568.5 | 1310.8 | 959.6 | 537.1 | 1007.6 | 884.5 | 760.6 | 875.3 | 411.3 | 986.1 | 849.6 | 30.8 |
| 12.0 | 1126.6 | 566.1 | 1260.8 | 1051.8 | 631.7 | 1031.7 | 882.7 | 728.5 | 962.5 | 438.3 | 1029.5 | 882.8 | 29.2 |
| 14.0 | 1000.9 | 404.4 | 896.8 | 1125.5 | 619.3 | 803.8 | 955.7 | 388.7 | 696.1 | 250.2 | 777.7 | 719.9 | 38.8 |
| 16.0 | 713.3 | 256.2 | 593.1 | 1032.5 | 537.2 | 627.3 | 842.8 | 240.1 | 541.5 | 184.8 | 619.3 | 562.6 | 46.1 |

TABLE 63-continued

Plasma concentration (ng/ml) profiles of the metformin determined
at different time points after a single dose of the test formulation
is orally administered to different subjects under fasting condition.

| Time | Subject ID No. | | | | | | | | | | | | CV |
| (hr) | 2 | 4 | 6 | 7 | 8 | 9 | 10 | 11 | 12 | 13 | 14 | Mean | % |
|---|---|---|---|---|---|---|---|---|---|---|---|---|---|
| 20.0 | 314.8 | 113.8 | 271.6 | 603.8 | 485.9 | 290.3 | 392.5 | 133.9 | 308.2 | 140.2 | 372.5 | 311.6 | 48.5 |
| 24.0 | 173.0 | 69.1 | 117.9 | 299.9 | 310.0 | 112.1 | 240.3 | 68.5 | 203.5 | 93.0 | 229.7 | 174.3 | 50.8 |
| 28.0 | 78.0 | 31.4 | 52.4 | 191.3 | 107.5 | 42.8 | 112.3 | 29.6 | 123.9 | 53.1 | 106.4 | 84.4 | 58.5 |
| 36.0 | 24.2 | 0.0 | 0.0 | 44.3 | 25.8 | 0.0 | 26.0 | 0.0 | 39.0 | 20.6 | 27.7 | 18.9 | 86.8 |

As shown in Table 36, the maximum plasma concentration ($T_{max}$) of metformin for each subject after oral administration of a single dose of the oral dosage form of formulation T ranges approximately 8.5-14 hours among different subjects after oral administration, with the mean plasma concentration peaking at 12 hours after oral administration.

Furthermore, the key pharmacokinetics (PK) parameters for formulation T after oral administration is further summarized in Table 64.

TABLE 64

Pharmacokinetics (PK) parameters for formulation T.

| PK Parameters (Units) | Test product (T) |
|---|---|
| $C_{max}$ (ng/ml) | 996.888 ± 225.0124 (22.57%) |
| $^{\#}T_{max}$ (hr) | 12.0 (8.5 – 14.0) |
| $AUC_{0-t}$ (hr*ng/mL) | 12070.934 ± 3098.2367 (25.67%) |
| $AUC_{0-\infty}$ (hr*ng/mL) | 12262.470 ± 3115.0755 (25.40%) |
| $t_{1/2}$ (hr) | 4.087 ± 0.8083 (19.78%) |
| $K_{el}$ (1/hr) | 0.1753 ± 0.03237 (18.47%) |
| AUC_%Extrap_obs (%) | 1.643 ± 0.5687 (34.61%) |

Note:
$^{\#}$ For $T_{max}$ median (min – max)

The mean plasma concentrations of metformin between the test formulation and the reference formulation are further compared.

Figure 3A:
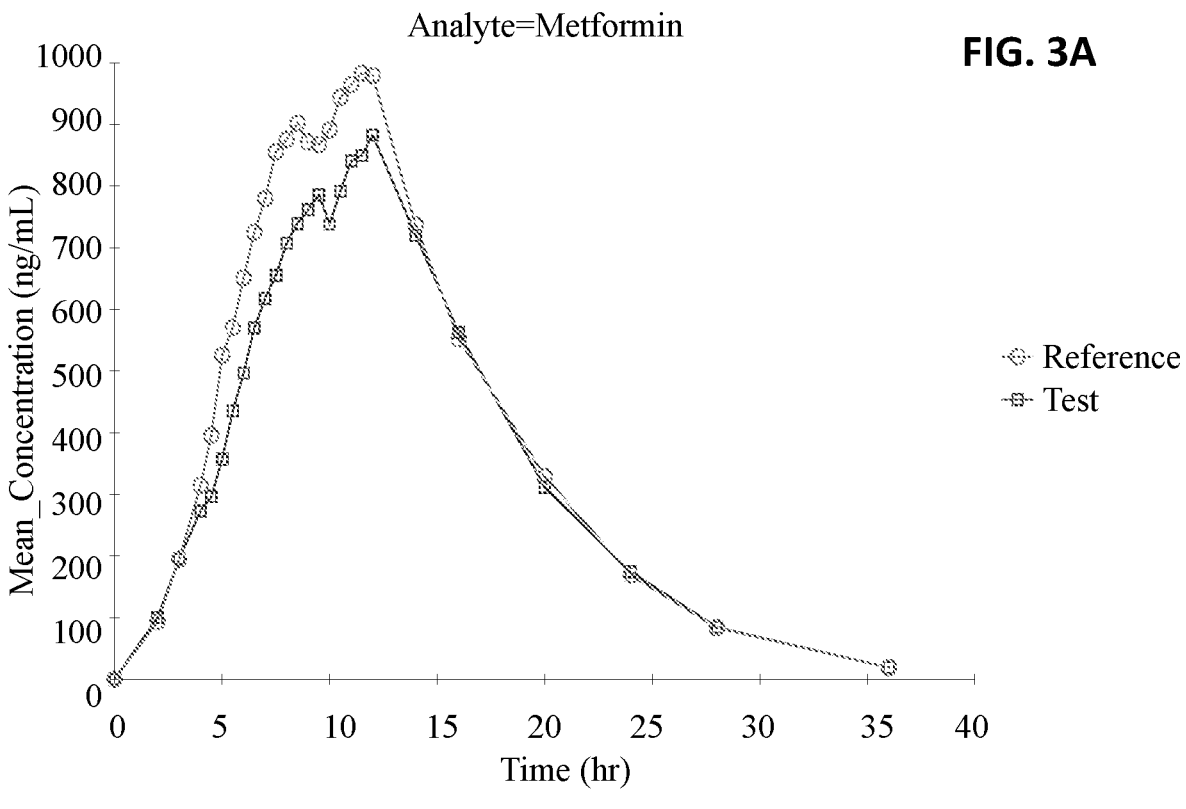
FIGS. 3A and 3B respectively show the linear and semilogarithmic plots of mean plasma concentrations of metformin HCl versus time for the reference formulation ("Reference") and the test formulation ("Test", i.e., Metformin HCl/Sitagliptin phosphate CR 1000/100 mg tablets formulation provided in Embodiment 1 of this present disclosure) in subjects under fasting condition.
Figure 3B:
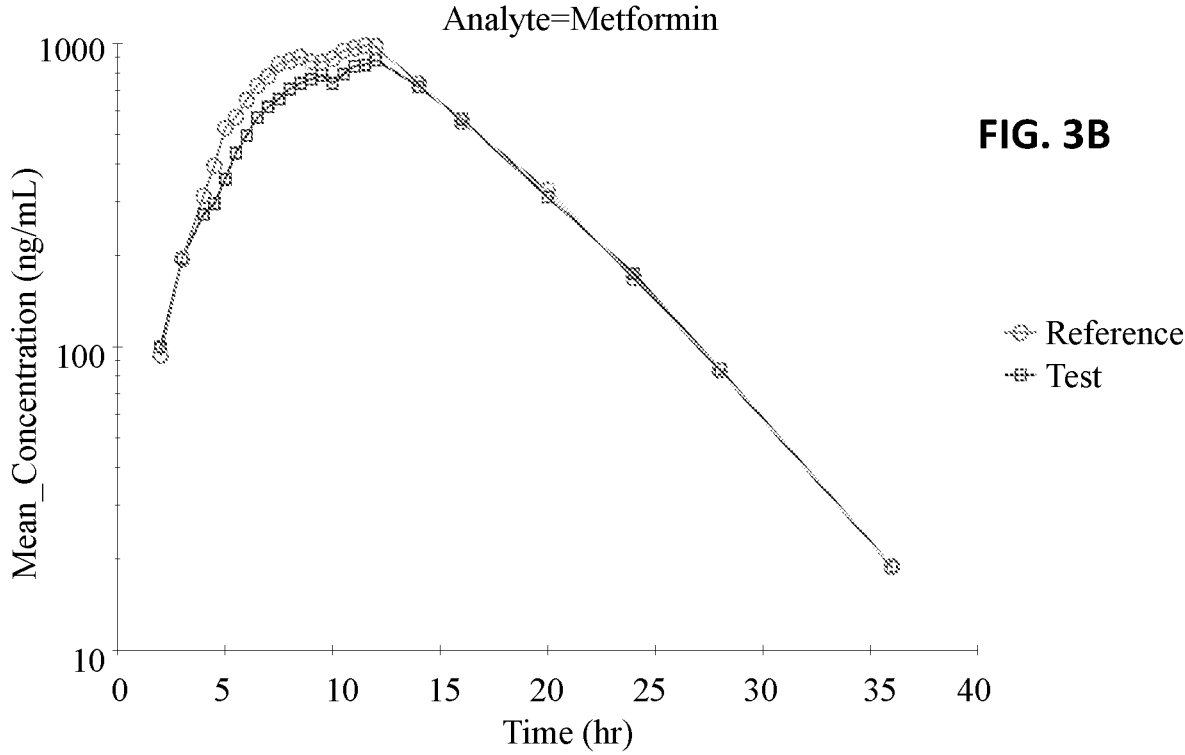

FIGS. 3A and 3B respectively show the linear and semi-logarithmic plots of mean plasma concentrations of metformin HCl versus time for the reference formulation ("Reference") and the test formulation ("Test", i.e., Metformin HCl/Sitagliptin phosphate CR 1000/100 mg tablets formulation provided in Embodiment 1 of this present disclosure) in subjects under fasting condition.

Figure 4A:
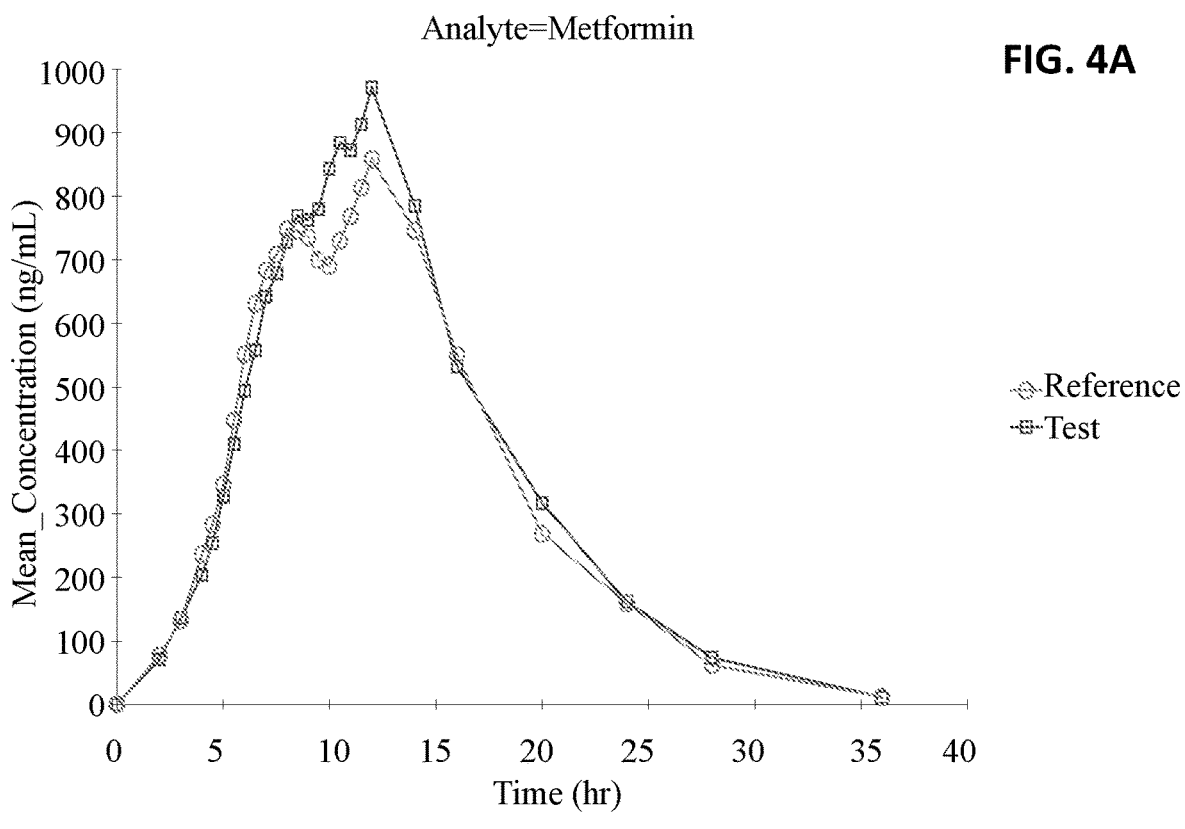
FIGS. 4A and 4B respectively show the linear and semilogarithmic plots of mean plasma concentrations of metformin HCl versus time for the reference formulation ("Reference") and the test formulation ("Test", i.e., Metformin HCl/Sitagliptin phosphate CR 1000/100 mg tablets formulation provided in Embodiment 1 of this present disclosure) in subjects under fed condition.
Figure 4B:
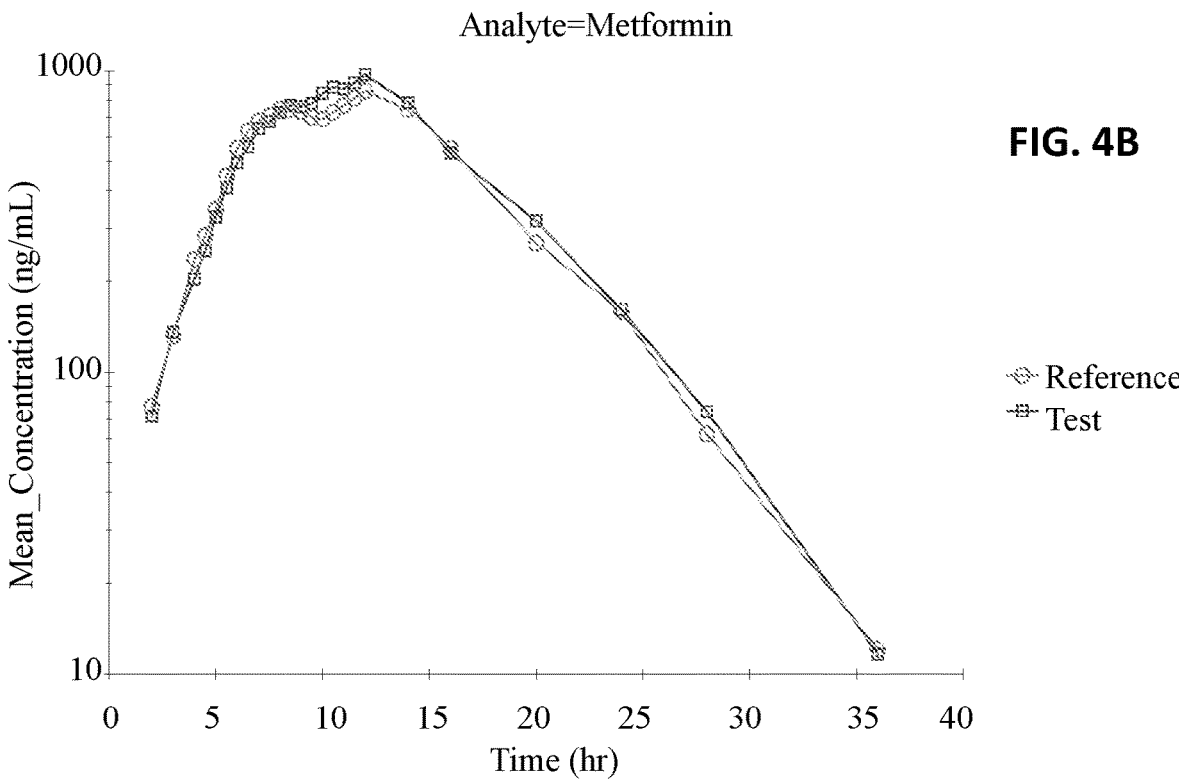

FIGS. 4A and 4B respectively show the linear and semi-logarithmic plots of mean plasma concentrations of metformin HCl versus time for the reference formulation ("Reference") and the test formulation ("Test", i.e., Metformin HCl/Sitagliptin phosphate CR 1000/100 mg tablets formulation provided in Embodiment 1 of this present disclosure) in subjects under fed condition.

It should be noted that these above embodiments and examples of the pharmaceutical composition comprising metformin HCl and sitagliptin phosphate serve as illustrating examples only and shall not be interpreted as limitations of the scope.

All references cited in the present disclosure are incorporated by reference in their entirety. Although specific embodiments have been described above in detail, the description is merely for purposes of illustration. It should be appreciated, therefore, that many aspects described above are not intended as required or essential elements unless explicitly stated otherwise.

Various modifications of, and equivalent acts corresponding to, the disclosed aspects of the exemplary embodiments, in addition to those described above, can be made by a person of ordinary skill in the art, having the benefit of the present disclosure, without departing from the spirit and scope of the disclosure defined in the following claims, the scope of which is to be accorded the broadest interpretation so as to encompass such modifications and equivalent structures.

The invention claimed is:

1. An oral dosage form of a pharmaceutical composition for managing diabetes or prediabetes in a subject, comprising:
   a core portion comprising a therapeutically effective amount of metformin hydrochloride (metformin HCl);
   an outer portion comprising at least one non-biguanide antidiabetic agent, each at a therapeutically effective amount; and
   a controlled membrane film encapsulating the core portion and sandwiched between the core portion and the outer portion, wherein the controlled membrane film is provided with at least one passageway configured to allow the metformin hydrochloride to release out of the core portion therethrough when the oral dosage form is in an aqueous environment;
   wherein:
      the oral dosage form has a dissolution profile such that upon dissolving in a medium with a pH of approximately 6.8 at approximately 37° C.:
         less than 50% of the metformin hydrochloride is released from the oral dosage form at approximately 8 hours; and
         no less than 80% of the metformin hydrochloride is released from the oral dosage form at approximately 24 hours.

2. The oral dosage form of claim 1, wherein upon dissolving in a medium with a pH of approximately 6.8 at approximately 37° C.:
   approximately 45-70% of the metformin is released from the oral dosage form at approximately 12 hours.

3. The oral dosage form of claim 2, wherein upon dissolving in a medium with a pH of approximately 6.8 at approximately 37° C.:
   approximately 5-10% of the metformin is released from the oral dosage form at approximately 2 hours.

4. The oral dosage form of claim 1, wherein the core portion comprises approximately 250-2000 mg of metformin HCl.

5. The oral dosage form of claim 1, wherein the at least one non-biguanide antidiabetic agent comprises at least one DDP-4 inhibitor or a pharmaceutically acceptable salt thereof, wherein:

the at least one DDP-4 inhibitor comprises one or more of sitagliptin, saxagliptin, linagliptin, alogliptin, vildagliptin, gemigliptin, anagliptin, teneligliptin, trelagliptin, omarigliptin, evogliptin, gosogliptin, dutogliptin, or berberine.

6. The oral dosage form of claim 5, wherein the at least one non-biguanide antidiabetic agent comprises approximately 25-200 mg of sitagliptin phosphate.

7. The oral dosage form of claim 6, wherein when the oral dosage form is tested in a USP Type I apparatus at approximately 75 rpm at approximately 37° C. in 900 ml of 0.025 mol/mL sodium chloride solution:

more than 85% of the sitagliptin phosphate is released at approximately 60 min after testing.

8. The oral dosage form of claim 7, wherein when tested in a USP Type I apparatus at approximately 75 rpm at approximately 37° C. in 900 ml of 0.025 mol/mL sodium chloride solution:

more than 25% of the sitagliptin phosphate is released at approximately 10 min after testing.

9. The oral dosage form of claim 1, wherein the at least one non-biguanide antidiabetic agent comprises one or more of:

a sulfonylurea or a pharmaceutically acceptable salt thereof;

a meglitinide or a pharmaceutically acceptable salt thereof;

a thiazolidinedione or a pharmaceutically acceptable salt thereof;

a sodium-glucose transporter 2 (SGLT2) inhibitor or a pharmaceutically acceptable salt thereof; or an alpha-glucosidase inhibitor or a pharmaceutically acceptable salt thereof.

10. The oral dosage form of claim 9, wherein the at least one non-biguanide antidiabetic agent has an immediate release formulation and comprises one of:

dapagliflozin having a dosage strength of approximately 2.5-10 mg;

empagliflozin having a dosage strength of approximately 2.5-25 mg;

glipizide having a dosage strength of approximately 1.25-10 mg;

glyburide having a dosage strength of approximately 1.25-10 mg;

repaglinide having a dosage strength of approximately 0.5-5 mg;

nateoglinide having a dosage strength of approximately 30-60 mg;

pioglitazone having a dosage strength of approximately 15-45 mg;

rosiglitazone having a dosage strength of approximately 1-4 mg;

acarbose having a dosage strength of approximately 12.5-100 mg; or miglitol having a dosage strength of approximately 12.5-100 mg.

11. The oral dosage form of claim 1, wherein the at least one passageway consists of two passageways, respectively arranged on two opposing sides of the controlled membrane film.

* * * * *